(12) United States Patent
Moffitt et al.

(10) Patent No.: US 8,131,358 B2
(45) Date of Patent: *Mar. 6, 2012

(54) SYSTEM AND METHOD FOR MAINTAINING A DISTRIBUTION OF CURRENTS IN AN ELECTRODE ARRAY USING INDEPENDENT VOLTAGE SOURCES

(75) Inventors: Michael Moffitt, Valencia, CA (US); David K. L. Peterson, Saugus, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 355 days.

This patent is subject to a terminal disclaimer.

(21) Appl. No.: 12/508,290

(22) Filed: Jul. 23, 2009

(65) Prior Publication Data

US 2010/0023070 A1     Jan. 28, 2010

Related U.S. Application Data

(62) Division of application No. 12/507,260, filed on Jul. 22, 2009, now Pat. No. 8,055,337.

(60) Provisional application No. 61/083,491, filed on Jul. 24, 2008.

(51) Int. Cl.
*A61N 1/00* (2006.01)

(52) U.S. Cl. .......................................................... 607/2
(58) Field of Classification Search ........................ 607/2
See application file for complete search history.

(56) References Cited

U.S. PATENT DOCUMENTS

| 3,646,940 A | 3/1972 | Timm et al. |
|---|---|---|
| 3,724,467 A | 4/1973 | Avery et al. |
| 3,822,708 A | 7/1974 | Zilber |
| 5,167,229 A | 12/1992 | Peckham et al. |
| 5,285,781 A | 2/1994 | Brodard |
| 5,417,719 A | 5/1995 | Hull et al. |

(Continued)

FOREIGN PATENT DOCUMENTS

EP     0459945 A1     12/1991

(Continued)

OTHER PUBLICATIONS

PCT International Search Report for PCT/US2009/051361, Applicant: Boston Scientific Neuromodulation Corporation, Form PCT/ISA/210 and 220, dated Oct. 19, 2009 (7 pages).

(Continued)

*Primary Examiner* — George Manuel
(74) *Attorney, Agent, or Firm* — Vista IP Law Group LLP

(57) ABSTRACT

In one technique, a desired electrical current distribution on at least three active electrodes is selected. An electrical energy perturbation is generated on at least one electrode. A current-to-voltage relationship at each active electrode is estimated based on the energy perturbation. The current-to-voltage relationship for each active electrode takes into account current flow through other active electrodes. The voltage distribution necessary to achieve the desired current distribution is determined based on the estimated current-to-voltage relationship. Voltage-regulated energy is conveyed between the electrodes and tissue in accordance with the determined electrical voltage distribution. In another technique, an electrical energy perturbation on at least one of the electrodes is generated. Network resistances for each of at least three active electrodes are computed in response to the energy perturbation. The network resistances represent the resistances between the electrodes and common node to which the electrodes are connected.

25 Claims, 9 Drawing Sheets

U.S. PATENT DOCUMENTS

| | | | |
|---|---|---|---|
| 5,501,703 A | 3/1996 | Holsheimer et al. | |
| 5,522,865 A | 6/1996 | Schulman et al. | |
| 5,531,774 A | 7/1996 | Schulman et al. | |
| 5,562,718 A | 10/1996 | Palermo | |
| 5,569,307 A | 10/1996 | Schulman et al. | |
| 5,571,148 A | 11/1996 | Loeb et al. | |
| 5,601,617 A | 2/1997 | Loeb et al. | |
| 5,603,726 A | 2/1997 | Schulman et al. | |
| 5,609,616 A | 3/1997 | Schulman et al. | |
| 5,626,629 A | 5/1997 | Faltys et al. | |
| 5,643,330 A | 7/1997 | Holsheimer et al. | |
| 5,649,970 A | 7/1997 | Loeb et al. | |
| 5,769,875 A | 6/1998 | Peckham et al. | |
| 5,776,171 A | 7/1998 | Peckham et al. | |
| 5,776,172 A | 7/1998 | Schulman et al. | |
| 5,876,425 A | 3/1999 | Gord et al. | |
| 5,895,416 A | 4/1999 | Barreras, Sr. et al. | |
| 5,938,690 A | 8/1999 | Law et al. | |
| 5,938,691 A | 8/1999 | Schulman et al. | |
| 5,941,906 A | 8/1999 | Barreras, Sr. et al. | |
| 5,954,758 A | 9/1999 | Peckham et al. | |
| 6,002,966 A | 12/1999 | Loeb et al. | |
| 6,026,328 A | 2/2000 | Peckham et al. | |
| 6,052,624 A | 4/2000 | Mann | |
| 6,163,725 A | 12/2000 | Peckham et al. | |
| 6,192,279 B1 | 2/2001 | Barreras, Sr. et al. | |
| 6,219,580 B1 | 4/2001 | Faltys et al. | |
| 6,366,815 B1 | 4/2002 | Haugland et al. | |
| 6,381,496 B1 | 4/2002 | Meadows et al. | |
| 6,393,325 B1 | 5/2002 | Mann et al. | |
| 6,487,446 B1 | 11/2002 | Hill et al. | |
| 6,507,757 B1 | 1/2003 | Swain et al. | |
| 6,516,227 B1 | 2/2003 | Meadows et al. | |
| 6,553,263 B1 | 4/2003 | Meadows et al. | |
| 6,587,724 B2 | 7/2003 | Mann | |
| 6,609,032 B1 | 8/2003 | Woods et al. | |
| 6,622,048 B1 | 9/2003 | Mann et al. | |
| 6,690,973 B2 | 2/2004 | Hill et al. | |
| 6,718,210 B1 | 4/2004 | Peckham et al. | |
| 6,731,986 B2 | 5/2004 | Mann | |
| 6,760,626 B1 | 7/2004 | Boveja | |
| 6,879,860 B2 | 4/2005 | Wakefield et al. | |
| 6,882,887 B1 | 4/2005 | Shelchok et al. | |
| 6,895,280 B2 | 5/2005 | Meadows et al. | |
| 6,909,917 B2 | 6/2005 | Woods et al. | |
| 6,993,384 B2 | 1/2006 | Bradley et al. | |
| 7,146,223 B1 | 12/2006 | King | |
| 7,177,690 B2 | 2/2007 | Woods et al. | |
| 7,177,691 B2 | 2/2007 | Meadows et al. | |
| 7,184,828 B2 | 2/2007 | Hill et al. | |
| 7,184,836 B1 | 2/2007 | Meadows et al. | |
| 7,212,854 B2 | 5/2007 | Kovak et al. | |
| 7,248,929 B2 | 7/2007 | Meadows et al. | |
| 7,295,878 B1 | 11/2007 | Meadows et al. | |
| 7,317,948 B1 | 1/2008 | King et al. | |
| 7,389,140 B1 * | 6/2008 | Kroll | 607/9 |
| 7,496,404 B2 | 2/2009 | Meadows et al. | |
| 7,539,538 B2 | 5/2009 | Parramon et al. | |
| 7,555,346 B1 | 6/2009 | Woods et al. | |
| 2001/0000187 A1 | 4/2001 | Peckham et al. | |
| 2001/0034542 A1 | 10/2001 | Mann | |
| 2002/0193843 A1 | 12/2002 | Hill et al. | |
| 2003/0114899 A1 | 6/2003 | Woods et al. | |
| 2003/0120323 A1 | 6/2003 | Meadows et al. | |
| 2003/0139781 A1 | 7/2003 | Bradley et al. | |
| 2003/0191504 A1 | 10/2003 | Meadows et al. | |
| 2003/0195581 A1 | 10/2003 | Meadows et al. | |
| 2003/0195582 A1 | 10/2003 | Mann | |
| 2004/0034394 A1 | 2/2004 | Woods et al. | |
| 2004/0082980 A1 | 4/2004 | Mouine et al. | |
| 2004/0111118 A1 | 6/2004 | Hill et al. | |
| 2004/0167585 A1 | 8/2004 | Kovak et al. | |
| 2004/0181266 A1 | 9/2004 | Wakefield et al. | |
| 2005/0107841 A1 | 5/2005 | Meadows et al. | |
| 2005/0107845 A1 | 5/2005 | Wakefield et al. | |
| 2005/0125833 A1 | 6/2005 | Nathan et al. | |
| 2005/0143781 A1 | 6/2005 | Carbunaru et al. | |
| 2005/0203588 A1 | 9/2005 | King | |
| 2005/0209655 A1 | 9/2005 | Bradley et al. | |
| 2005/0245987 A1 | 11/2005 | Woods et al. | |
| 2005/0267546 A1 | 12/2005 | Parramon et al. | |
| 2007/0156207 A1 | 7/2007 | Kothandaraman et al. | |
| 2007/0185551 A1 | 8/2007 | Meadows et al. | |
| 2007/0208381 A1 | 9/2007 | Hill et al. | |
| 2007/0265679 A1 | 11/2007 | Bradley et al. | |
| 2007/0276450 A1 | 11/2007 | Meadows et al. | |
| 2007/0293914 A1 | 12/2007 | Woods et al. | |
| 2008/0071325 A1 | 3/2008 | Bradley | |
| 2008/0215119 A1 | 9/2008 | Woods et al. | |
| 2008/0221637 A1 | 9/2008 | Woods et al. | |
| 2009/0062883 A1 | 3/2009 | Meadows et al. | |
| 2009/0240302 A1 | 9/2009 | Woods et al. | |
| 2010/0010566 A1 | 1/2010 | Thacker et al. | |

FOREIGN PATENT DOCUMENTS

| | | |
|---|---|---|
| EP | 0774993 | 12/1995 |
| EP | 0741592 B1 | 5/2000 |
| EP | 1244496 | 6/2001 |
| EP | 0823188 B1 | 7/2001 |
| EP | 1322381 | 4/2002 |
| EP | 1328315 | 4/2002 |
| EP | 0948373 B1 | 9/2004 |
| EP | 1608431 | 9/2004 |
| EP | 1848493 | 7/2006 |
| EP | 0974376 B1 | 11/2007 |
| WO | WO 95/19804 A1 | 7/1995 |
| WO | WO 95/33516 A1 | 12/1995 |
| WO | WO 96/34508 A1 | 10/1996 |
| WO | WO 96/39005 A1 | 12/1996 |
| WO | WO 98/30279 A1 | 7/1998 |
| WO | WO 99/66982 A1 | 12/1999 |
| WO | WO 01/39831 A1 | 6/2001 |
| WO | WO 01/43818 A1 | 6/2001 |
| WO | WO 02/26319 A1 | 4/2002 |
| WO | WO 02/32501 A1 | 4/2002 |
| WO | WO 2004/080532 A1 | 9/2004 |
| WO | WO 2006/073393 A1 | 7/2006 |
| WO | WO 2006/073405 A2 | 7/2006 |
| WO | WO 2006/112852 A2 | 10/2006 |

OTHER PUBLICATIONS

PCT Written Opinion of the International Search Authority for PCT/US2009/051361, Applicant: Boston Scientific Neuromodulation Corporation, Form PCT/ISA/237, dated Oct. 19, 2009 (7 pages).

PCT International Preliminary Report on Patentability (Chapter I of the Patent Cooperation Treaty) for PCT/US2009/051361, Applicant: Boston Scientific Neuromodulation Corporation, Form PCT/IB/326 and 373, dated Feb. 3, 2011 (9 pages).

* cited by examiner

SYSTEM AND METHOD FOR MAINTAINING A DISTRIBUTION OF CURRENTS IN AN ELECTRODE ARRAY USING INDEPENDENT VOLTAGE SOURCES

RELATED APPLICATION

The present application is a divisional of U.S. patent application Ser. No. 12/507,260, filed Jul. 22, 2009, which claims the benefit under 35 U.S.C. §119(e) of Provisional Application Ser. No. 61/083,491, filed Jul. 24, 2008, which is incorporated hereby reference in its entirety.

FIELD OF THE INVENTION

The present invention relates to tissue stimulation systems, and more particularly, to a system and method for stimulating neural fibers.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device, such as a handheld patient programmer, to remotely instruct the neurostimulator to generate electrical stimulation pulses in accordance with selected stimulation parameters.

Electrical stimulation energy may be delivered from the neurostimulator to the electrodes in the form of an electrical pulsed waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, width, and rate of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different fractionalized electrode configurations.

As briefly discussed above, a hand-held programmer can be used to instruct the neurostimulator to generate electrical stimulation pulses in accordance with the selected stimulation parameters. Typically, the stimulation parameters programmed into the neurostimulator can be adjusted by manipulating controls on the hand-held programmer to modify the electrical stimulation provided by the neurostimulator system to the patient. However, the number of electrodes available, combined with the ability to generate a variety of complex stimulation pulses, presents a huge selection of stimulation parameter sets to the clinician or patient.

To facilitate such selection, the clinician generally programs the neurostimulator through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback or other means and to subsequently program the neurostimulator with the optimum stimulation parameter set or sets, which will typically be those that stimulate all of the target tissue in order to provide the therapeutic benefit, yet minimizes the volume of non-target tissue that is stimulated. The computerized programming system may be operated by a clinician attending the patient in several scenarios.

For example, in order to achieve an effective result from SCS, the lead or leads must be placed in a location, such that the electrical stimulation will cause paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neurostimulator to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neurostimulator, with a set of stimulation parameters that best addresses the painful site. Thus, the navigation session may be used to pinpoint the stimulation region or areas correlating to the pain. Such programming ability is particularly advantageous for targeting the tissue during implantation, or after implantation should the leads gradually or unexpectedly move that would otherwise relocate the stimulation energy away from the target site. By reprogramming the neurostimulator (typically by independently varying the stimulation energy on the electrodes), the stimulation region can often be moved back to the effective pain site without having to re-operate on the patient in order to reposition the lead and its electrode array. When adjusting the stimulation region relative to the tissue, it is desirable to make small changes in the proportions of current, so that changes in the spatial recruitment of nerve fibers will be perceived by the patient as being smooth and continuous and to have incremental targeting capability.

Electrical stimulation energy may be delivered from the neurostimulator to the electrodes using one or more current-controlled sources for providing stimulation pulses of a specified and known current (i.e., current regulated output pulses), or one or more voltage-controlled sources for providing stimulation pulses of a specified and known voltage (i.e., voltage regulated output pulses).

For example, the Precision® neurostimulator, marketed by Boston Scientific Neuromodulation Corporation, has a constant current source hardware platform with sixteen independent current sources that can independently deliver constant current at different magnitudes to any combination of electrodes over multiple channels. As another example, the Bion® microstimulator, marketed by Boston Scientific Neuromodulation Corporation, has a simpler, but smaller, constant current source hardware platform that can deliver current at equal magnitudes between two electrodes over a single channel. The Synergy® and Restore® neurostimulators, marketed by Medtronic, Inc., deliver electrical energy at a constant voltage, with both neurostimulators having a single voltage source at any point time. The Genesis® and EON® neurostimulators, marketed by Advanced Neuromodulation Systems, have single constant current sources.

In single source systems, whether current or voltage regulated, the spatial recruitment of nerve fibers using stimulation pulses is subject to variations of current-to-voltage relationships (i.e., impedance of the tissue, electrode, and electrode-tissue interface), since the electrical current cannot be adjusted amongst multiple electrodes in response to such current-to-voltage relationship variations. With respect to multiple source systems, the spatial recruitment of nerve fibers using voltage regulated output pulses is more subject to current-to-voltage relationship variations than the spatial stimulation of nerve fibers using current regulated output pulses. In particular, when output pulses are current regulated on each active electrode, the current is automatically maintained on the respective active electrode regardless of impedance variations. Thus, because current, as opposed to voltage, is most directly related to stimulation strength, the use of current regulated output pulses reduces the sensitivity of the spatial recruitment of nerve fibers to impedance variations.

This is not the case, however, when output pulses are voltage regulated, since the current on each active electrode will vary with the change in impedance. Even a small change in the current distribution on the active electrodes can change the spatial recruitment of nerve fibers causing a reduction in therapeutic efficacy and/or patient comfort. In part, this is because the clinical usage range for stimulation (difference between perception and maximum tolerated amplitude) is only a fraction of the therapeutic stimulation amplitude.

With respective to system having multiple sources, changes in impedance will cause changes in the distribution of current among electrodes in a voltage regulated system even if each electrode has a dedicated voltage regulated output. These impedance changes can occur over time as the electrodes encapsulate or in the short term as a result of the encapsulation process, changes at the electrode-tissue interface, patient movement, respiration, arterial perfusion, postural changes. Thus, without some means of adjusting the output voltage distribution on all active electrodes based on impedance variations, the stimulation pattern can change, resulting in reduced therapeutic efficacy.

A method and means for adjusting the voltages on all active electrodes to generate a desired current distribution on the active electrodes would help maintain therapy in the presence of impedance changes and allow new distributions of current to be generated when adjusting the stimulation region relative to the tissue.

SUMMARY OF THE INVENTION

In accordance with a first aspect of the present inventions, a method of performing a medical procedure using a plurality of electrodes implanted within tissue of a patient is provided. The method comprises comprising selecting a desired electrical current distribution on at least three active ones of the electrodes. As one example, the desired electrical current distribution can be selected during a current steering procedure; that is, modifying a first desired electrical current distribution to a second desired electrical current distribution. In another example, the desired current distribution can be selected as a result of uniformly changing the amplitude of the total current flowing through the active electrodes. The method further comprises generating an electrical energy perturbation (e.g., a voltage-regulated perturbation) on at least one of the plurality of electrodes.

The method further comprises estimating a current-to-voltage relationship at each of the active electrodes based on the generated electrical energy perturbation. Significantly, the current-to-voltage relationship for each of the active electrodes takes into account electrical current flow through others of the active electrodes. In one method, the current-to-voltage relationship is estimated at a zero operating point of the voltage-regulated electrical energy. In this case, the electrical energy perturbation may be generated in the absence of the conveyed voltage-regulated electrical energy. In another method, the current-to-voltage relationship is estimated at a non-zero operating point of the voltage-regulated electrical energy. In this case, the electrical energy perturbation may be generated during the conveyance of the voltage-regulated electrical energy.

The method further comprises determining an electrical voltage distribution on the active electrodes necessary to achieve the desired electrical current distribution on the active electrodes, wherein the electrical voltage distribution is based on the estimated current-to-voltage relationship. One method further comprises measuring one or more electrical parameters in response to generating the electrical energy perturbation. In this case, the estimation of the current-to-voltage relationship at each of the active electrodes is based on the electrical parameter measurement.

The measured electrical parameter(s) may, e.g., comprise a plurality of interelectrode impedances between the active electrodes. In this case, the estimation of the current-to-voltage relationship at each of the active electrodes may comprise computing network resistances (representing the resistances between the respective active electrodes and a common node to which the active electrodes are connected in parallel) for each of the active electrodes based on the interelectrode impedances. The measured electrical parameter(s) may also, e.g., comprise a plurality of field potentials at the at least three electrodes and a plurality of monopolar impedances of the at least three electrodes.

The method further comprises conveying voltage-regulated electrical energy between the at least three electrodes and the tissue (e.g., spinal cord tissue) in accordance with the determined electrical voltage distribution. In one method, the electrical energy takes the form of an electrical pulse waveform that stimulates the tissue.

In accordance with a second aspect of the present inventions, a neurostimulation system is provided. The neurostimulation system comprises a plurality of electrodes configured for being placed in contact with tissue, analog output circuitry configured generating an electrical energy perturbation on at least one of the plurality of electrodes, and processing circuitry (which may include one processor or multiple processors) configured for selecting a desired electrical current distribution on at least three active ones of the plurality of electrodes, estimating a current-to-voltage relationship at each of the active electrodes based on the generated electrical energy perturbation, and determining an electrical voltage distribution on the active electrodes necessary to achieve the desired electrical current distribution on the active electrodes.

The electrical voltage distribution is based on the estimated current-to-voltage relationship, the current-to-voltage relationship for each of the active electrodes takes into account electrical current flow through others of the active electrodes, and the analog output circuitry is configured for conveying voltage-regulated electrical energy between the active electrodes and the tissue in accordance with the determined electrical voltage distribution.

The desired electrical current distribution can be selected, the electrical energy perturbation can be generated, the current-to-voltage relationship estimated, and the electrical voltage distribution determined in the same manner described above. The neurostimulation system may further comprise monitoring circuitry configured for measuring one or more electrical parameters in response to the analog output circuitry generating the electrical energy perturbation, in which case, the processing circuitry may be configured for estimating the current-to-voltage relationship at each of the active electrodes based on the electrical parameter measurement in the manner described above. The electrical energy may be a tissue stimulating electrical pulse waveform. In one exemplary embodiment, the neurostimulation system may further comprise an implantable neurostimulator containing the analog output circuitry, and an external controller containing the processing circuitry.

In accordance with a third aspect of the present inventions, a method of performing a medical procedure using a plurality of electrodes implanted within tissue of a patient is provided. The method comprises generating an electrical energy perturbation (e.g., a voltage regulated perturbation) on at least one of the plurality of electrodes, and computing network resistances for each of at least three active ones of the electrodes in response to the electrical energy perturbation. The network resistances represent the resistances between the respective active electrodes and a common node to which the active electrodes are connected in parallel.

In one method, the electrical energy perturbation creates a change in voltage drop between two of the active electrodes and a change in electrical current between the two active electrodes. In this case, the computation of the network resistance for each of the two active electrodes may comprise dividing a change in voltage on the respective active electrode by the change in the electrical current between the two electrodes. The voltage drop between the two active electrodes may be changed in a manner that maintains a voltage at the common node at the same value. In this case, the generation of the electrical energy perturbation may comprise generating oppositely polarized pulses at the two active electrodes.

Another method may comprise measuring interelectrode impedances between the active electrodes in response to generating the electrical energy perturbation, wherein the network resistances are computed based on the measured interelectrode impedances. In this case, interelectrode impedance for a respective active electrode may be computed by summing interelectrode impedances between each respective active electrode and two of the other active electrodes, subtracting the interelectrode impedance between the other two active electrodes from the sum, and dividing the result by two.

Another method further comprises determining an electrical voltage distribution on the active electrodes necessary to achieve a desired electrical current distribution on the active electrodes, or determining an electrical current distribution on the active electrodes necessary to achieve a desired voltage distribution on the active electrodes. In this case, the electrical voltage distribution or electrical current distribution is based on the computed network resistances.

Still another method comprises conveying electrical stimulation energy between the active electrodes and the tissue. In this case, the network resistances may be computed at a zero operating point of the conveyed electrical stimulation energy (e.g., the electrical energy perturbation may be generated in the absence of the conveyed electrical stimulation energy) or the network resistances may be computed at a non-zero operating point of the conveyed electrical stimulation energy (e.g., the electrical energy perturbation may be generated during the conveyance of the electrical stimulation energy).

In accordance with a fourth aspect of the present inventions, a neurostimulation system is provided. The neurostimulation system comprises a plurality of electrodes configured for being placed in contact with tissue, analog output circuitry configured generating an electrical energy perturbation on at least one of the plurality of electrodes, and processing circuitry configured for computing network resistances for each of at least three active ones of electrodes in response to the electrical energy perturbation, wherein the network resistances represent the resistances between the respective active electrodes and a common node to which the active electrodes are connected in parallel. The electrical energy perturbation generation and network resistance computing functions can be performed in the same manner described above. In one exemplary embodiment, the neurostimulation system may further comprise an implantable neurostimulator containing the analog output circuitry, and an external controller containing the processing circuitry.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
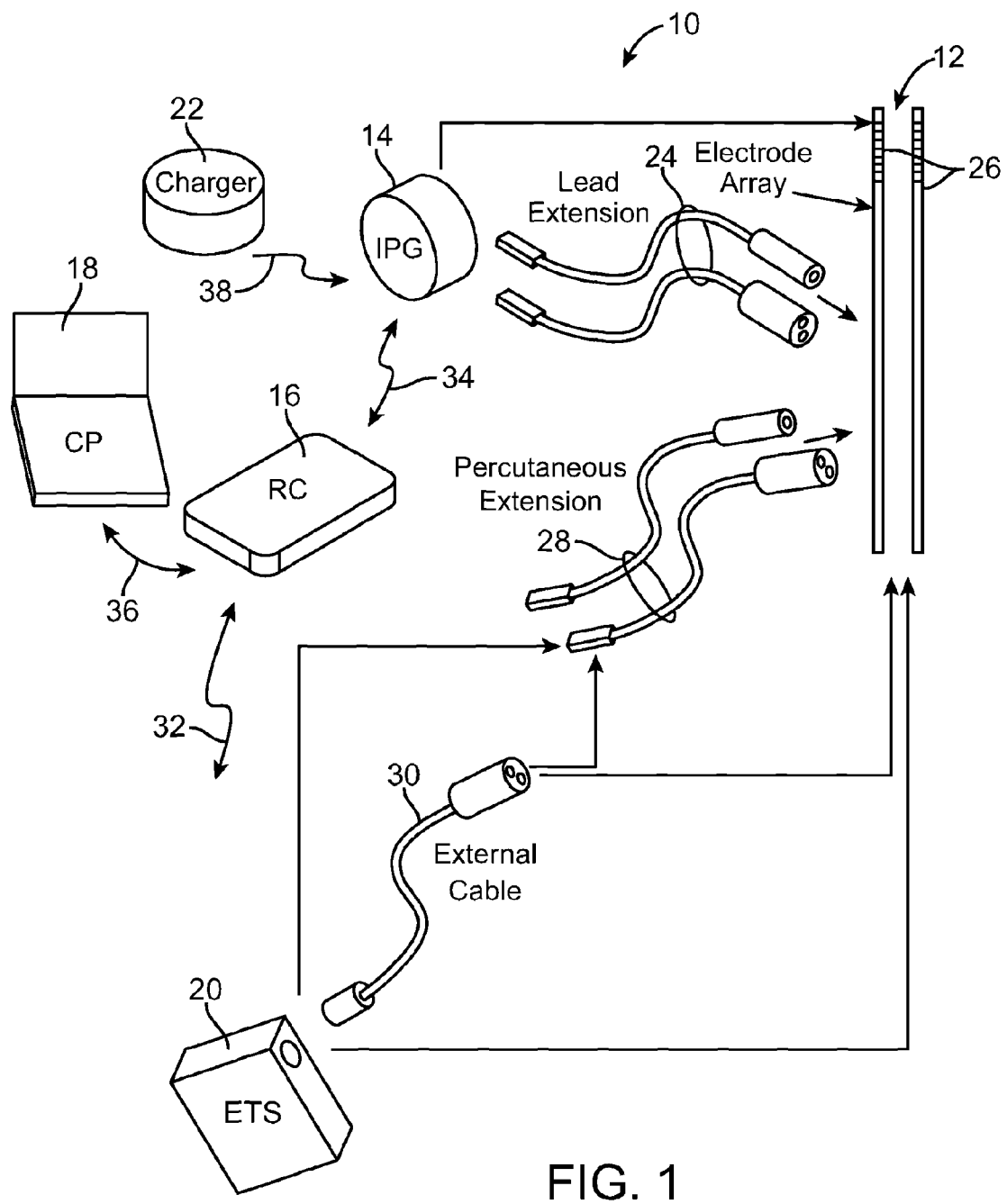
FIG. 1 is plan view of one embodiment of a spinal cord stimulation (SCS) system arranged in accordance with the present inventions.

Turning first to FIG. 1, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). For purposes of brevity and clarity, only the IPG 14 will be referred to hereafter. The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
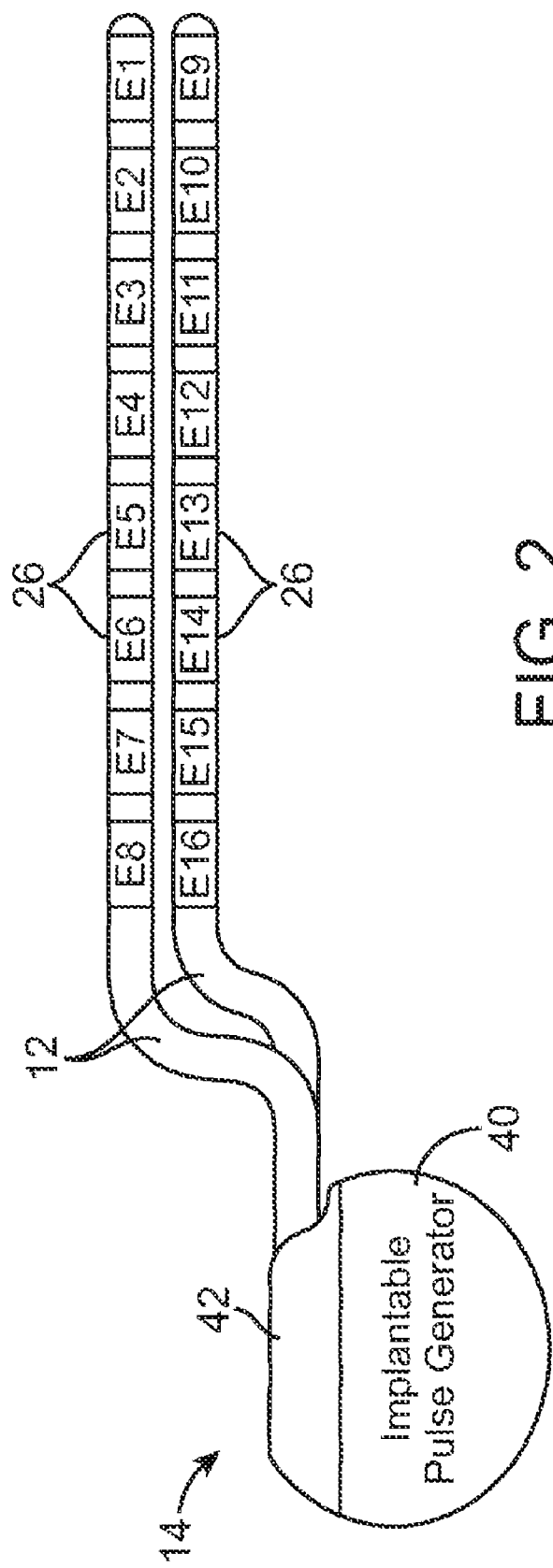
FIG. 2 is a plan view of an implantable pulse generator (IPG) and one embodiment of a stimulation lead used in the SCS system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 3:
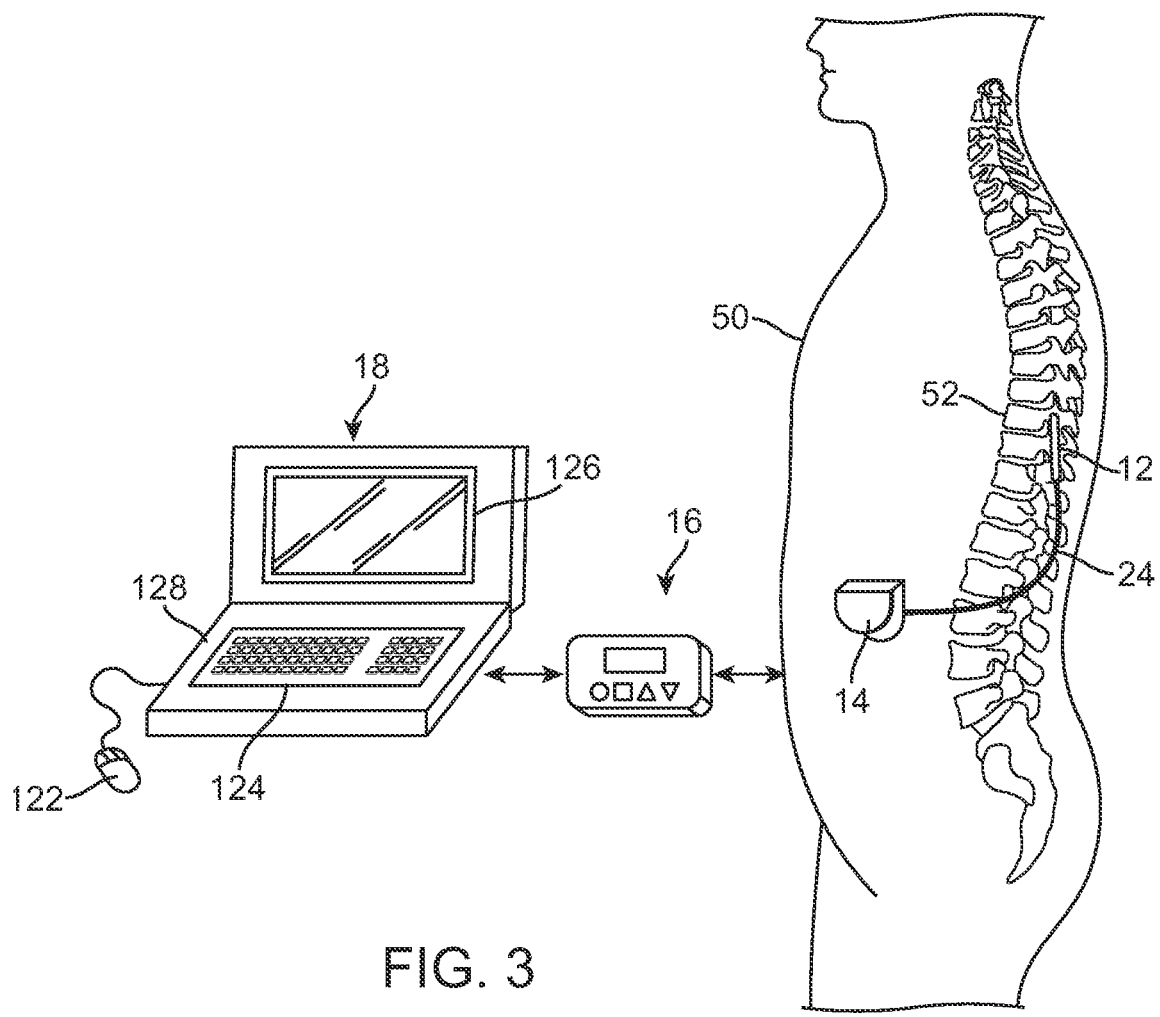
FIG. 3 is a plan view of the SCS system of FIG. 1 in use with a patient.

As shown in FIG. 3, the electrode leads 12 are implanted within the spinal column 52 of a patient 50. The preferred placement of the electrode leads 12 is adjacent, i.e., resting upon near, or upon the dura, adjacent to the spinal cord area to be stimulated. Due to the lack of space near the location where the electrode leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the electrode leads 12. As there shown, the CP 18 communicates with the IPG 14 via the RC 16.

As will be described in below, the IPG 14 includes independently controlled voltage-regulated sources, each capable of generating an electrical pulse at a known voltage value. Despite this, the system 10 is capable of achieving and maintaining a desired current distribution on the active electrodes 26 by adjusting the voltages on the active electrodes 26. In a sense, the system 10 is capable of mimicking control with multiple independently controlled current regulated sources by intelligently adjusting the voltage sources to control the currents through the electrodes 26 and control their relative stimulation strengths.

Notably, conventional wisdom dictates that the interelectrode voltage required to maintain a desired current between two electrodes can simply be computed by multiplying the desired current by the interelectrode impedance between the two electrodes. However, this is not the case when multiple independent voltage regulated sources are used with three or more active electrodes (one of which may be the IPG case), because the current on each active electrode is affected by the current through any other active electrode. That is, the presence of a field affects all contacts such that they are interrelated and cannot be considered to be completely independent. The embodiments described herein include approaches to account for the electrical relationships between active contacts.

That is, a higher impedance on one electrode will cause less current to flow to/from it, which, in turn, will affect the currents flowing from other electrodes, causing further imbalance in the ratios of currents among the electrodes. In addition to impedance changes, such an imbalance in the current ratios can also occur when the overall amplitude of the stimulation is increased or decreased. It is desirable to maintain the ratios of currents among the electrodes to avoid unbalancing the spatial recruitment of nerve fibers.

Independent voltage regulated outputs, however, cannot readily maintain the current distribution ratio if the current-to-voltage relationship (i.e., the tissue impedance, electrode impedance, and electrode-tissue interface impedance) is different among electrodes. The following example illustrates the problem in an electrical circuit analogy. Simple resistive loads are used in this example for illustrative purposes; however, the problem can be generalized to include more electrodes and complex current-to-voltage relationships, including interface potentials resulting from actual electrode-tissue interfaces.

Figure 4:
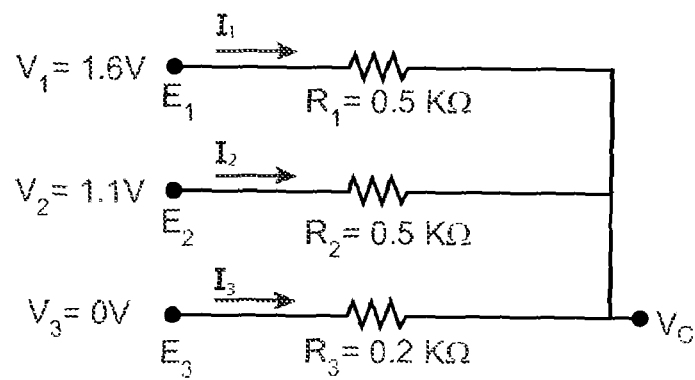
FIG. 4 is an exemplary three electrode resistive network on which a specific voltage distribution is applied.

Referring to FIG. 4, exemplary voltage regulated outputs on active electrodes $E_1$, $E_2$, and $E_3$ are respectively set to $V_1=1.6V$, $V_2=1.1V$, and $V_3=0V$ to provide efficacious therapy. The effective load in this example is a network of lumped resistances $R_1$, $R_2$, and $R_3$ connected to a voltage $V_C$ at a common node that is connected in parallel to the active electrodes $E_1$, $E_2$, and $E_3$. It should be noted that the resistive network can be generalized to include an arbitrary number of electrodes with more complex current-to-voltage relationships that include capacitive, reactive, non-linear, and active elements primarily found in electrode to tissue interfaces and tissue. The current-to-voltage relationship could include, for example, non-linear electrode polarization and electrochemical potential.

The common node voltage $V_C$ can be computed from Kirchhoff's current law using the following equation:

$$I_1 + I_2 + I_3 = \frac{V_1 - V_C}{R_1} + \frac{V_2 - V_C}{R_2} + \frac{V_3 - V_C}{R_3} = 0 \qquad [1]$$

Rearranging equation [1] to solve for the common node voltage $V_C$ provides:

$$V_C = \frac{V_1/R_1 + V_2/R_2 + V_3/R_3}{1/R_1 + 1/R_2 + 1/R_3} = \frac{1.6/0.5 + 1.1/0.5 + 0/0.2}{1/0.5 + 1/0.5 + 1/0.2} = \frac{32 + 2.2 + 0}{2 + 2 + 5} = \frac{5.4}{9} = 0.6 \text{ V} \qquad [2]$$

The currents flowing through each electrode can then be computed from Ohm's Law using the following equations:

$$I_1 = \frac{V_1 - V_C}{R_1} = \frac{1.6 - 0.6}{0.5} = \frac{1}{0.5} = 2 \text{ mA} \qquad [3]$$

$$I_2 = \frac{V_2 - V_C}{R_2} = \frac{1.1 - 0.6}{0.5} = \frac{0.5}{0.5} = 1 \text{ mA} \qquad [4]$$

$$I_3 = \frac{V_3 - V_C}{R_3} = \frac{0 - 0.6}{0.2} = \frac{-0.6}{0.2} = -3 \text{ mA} \qquad [5]$$

The current distribution from electrodes $E_1$, $E_2$, and $E_3$ required to provide therapy is thus: $I_1=2$ mA; $I_2=1$ mA, and $I_3=-3$ mA, respectively.

Figure 5:
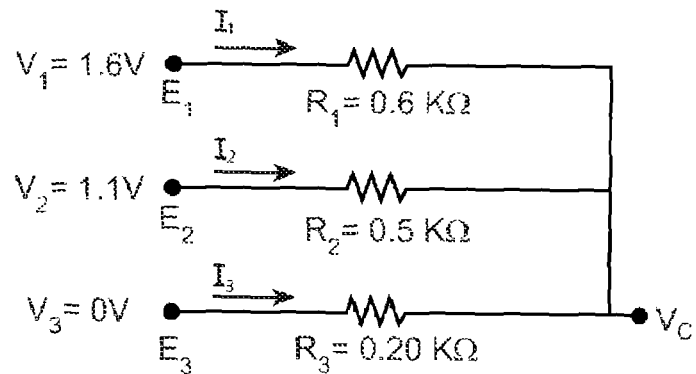
FIG. 5 is the resistive network of FIG. 4 on which another specific voltage distribution is applied.

However, if the tissue and/or electrode impedance on electrode $E_1$ increases slightly, the effective resistance $R_1$ will increase, thereby causing less current to flow through electrode $E_1$. A change in the network resistance $R_1$ also changes the common node voltage $V_C$, which affects the currents $I_2$ and $I_3$ flowing through the respective electrodes $E_2$ and $E_3$ as well. In other words, a change in impedance on one active electrode affects not just the current from the associated voltage regulated output, but it also unbalances the distribution of current on all other active electrodes. If the network resistance $R_1$ increased to 0.6 k$\Omega$, as shown in FIG. 5, the common node voltage $V_C$ can be recomputed using equation [2], as follows:

$$V_C = \frac{V_1/R_1 + V_2/R_2 + V_3/R_3}{1/R_1 + 1/R_2 + 1/R_3} =$$

$$\frac{1.6/0.6 + 1.1/0.5 + 0/0.2}{1/0.6 + 1/0.5 + 1/0.2} = \frac{2.67 + 2.2 + 0}{1.67 + 2 + 5} = \frac{4.87}{8.67} = 0.56 \text{ V}$$

The currents from each active electrode can then be recomputed using equations [3], [4], and [5], as follows:

$$I_1 = \frac{V_1 - V_C}{R_1} = \frac{1.6 - 0.56}{0.6} = \frac{1.04}{0.6} = 1.73 \text{ mA}$$

$$I_2 = \frac{V_2 - V_C}{R_2} = \frac{1.1 - 0.56}{0.5} = \frac{0.54}{0.5} = 1.08 \text{ mA}$$

$$I_3 = \frac{V_3 - V_C}{R_3} = \frac{0 - 0.56}{0.2} = \frac{-0.56}{0.2} = -2.81 \text{ mA}$$

As briefly discussed above, the solution allows adjustment of multiple independent voltage outputs to deliver a desired distribution of current through the active electrodes. This method first includes selecting a desired electrical current distribution on the active electrodes. For example, such a selection can occur during current steering (e.g., changing the from one electrical current distribution to another different electrical current distribution). The method further comprises generating an electrical energy perturbation (in the illustrated case, a voltage perturbation) on at least one of the electrodes, and estimating a current-to-voltage relationship at each of the active electrodes based on the generated electrical energy perturbation. Significantly, the current-to-voltage relationship for each active electrode is estimated in a manner that takes into account electrical current flow through the other active electrodes. Based on these estimated current-to-voltage relationships, the electrical voltage distribution on the active electrodes necessary to achieve the desired electrical current distribution on the active electrodes is then determined, and voltage-regulated electrical energy is then conveyed between the active electrodes and the tissue in accordance with the determined electrical voltage distribution.

In one method, interelectrode impedances are measured between the active electrodes, and lumped network resistances are computed for each of the active electrodes based on the interelectrode impedances. These lumped network resistances are then used to characterize the current-to-voltage relationships of the active electrodes from which the voltage distribution is determined to achieve the desired electrical current distribution.

In particular, the previously mentioned resistive networks of FIGS. 4 and 5 are used to represent the current-to-voltage relationships. In the example illustrated in FIG. 5, the increase in the resistance from 0.5 k$\Omega$ to 0.6 k$\Omega$ has respectively changed the current distribution from $I_1=2$ mA, $I_2=1$ mA, and $I_3=-3$ mA to $I_1=1.73$ mA, $I_2=1.08$ mA, and $I_3=-2.81$ mA. If the common node voltage $V_C$ is maintained at 0.6V, the current distribution will be restored back to its original value (i.e., $I_1=2$ mA, $I_2=1$ mA, and $I_3=-3$ mA). Although the solutions for the electrode voltages $V_1$, $V_2$, and $V_3$ will not be unique when maintaining the common node voltage $V_C$ at 0.6V, the new value of the voltage $V_1$ can be conveniently computed while maintaining the voltages $V_2$ and $V_3$ at their original values (i.e., without adjusting the voltages $V_2$ and $V_3$). In particular, assuming $R_1=0.6$ k$\Omega$, $V_C=0.6$V, and $I_1=2$ mA, the new value of the voltage $V_1$ can be recomputed using Kirchoff's Voltage Law with as follows:

$$V_1 = I_1 R_1 + V_C = (2 \text{ mA})(0.6 \text{ k}\Omega) + 0.6\text{V} = 1.2\text{V} + 0.6\text{V} = 0.8\text{V}$$

Using equation [2], the restoration of the common node voltage $V_C$ to 0.6V when voltage $V_1=1.8$V can be confirmed, as follows:

$$V_C = \frac{V_1/R_1 + V_2/R_2 + V_3/R_3}{1/R_1 + 1/R_2 + 1/R_3} = \frac{1.8/0.6 + 1.1/0.5 + 0/0.2}{1/0.6 + 1/0.5 + 1/0.2} = \frac{3 + 2.2 + 0}{1.67 + 2 + 5} = \frac{5.2}{8.67} = \frac{5.2}{8.67}$$

Using equations [3], [4], and [5], the restoration of the currents $I_1$, $I_2$, and $I_3$ when $V_1=1.8$V can be confirmed, as follows:

$$I_1 = \frac{V_1 - V_C}{R_1} = \frac{1.8 - 0.6}{0.6} = \frac{1.2}{0.6} = 2 \text{ mA}$$

$$I_2 = \frac{V_2 - V_C}{R_2} = \frac{1.1 - 0.6}{0.5} = \frac{0.5}{0.5} = 1. \text{ mA}$$

$$I_3 = \frac{V_3 - V_C}{R_3} = \frac{0 - 0.6}{0.2} = \frac{-0.6}{0.2} = -3 \text{ mA}$$

As discussed above in the background of the invention, the proportional distribution of current may become unbalanced if the overall amplitude of the stimulation is changed. As an example, if the clinician or patient wishes to increase the overall amplitude to 3.5 mA while maintaining this proportional distribution of current, the common node voltage $V_C$ will need to be changed in order to sink 3.5 mA into active electrode $E_3$ if $V_3=0V$. Using equation [5], the new common node voltage $V_C$ can be recomputed, as follows:

$$I_3 = \frac{V_3 - V_C}{R_3} = -3.5 \text{ mA} \Rightarrow V_C = V_3 - I_3 R_3 = 0 - (-3.5)(0.2) = 0.7 \text{ V}$$

To maintain the proportions of current on active electrodes $E_1$ and $E_2$:

$$I_1 = (2 \text{ mA})\left(\frac{3.5 \text{ mA}}{3 \text{ mA}}\right) = 2.3 \text{ mA}$$

$$I_2 = (1 \text{ mA})\left(\frac{3.5 \text{ mA}}{3 \text{ mA}}\right) = 1.17 \text{ mA}$$

Figure 6:
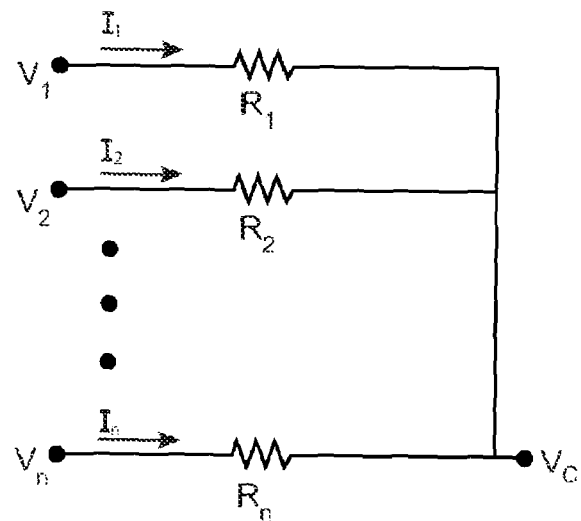
FIG. 6 is a generalized n electrode resistive network.

The new values of the voltage $V_1$ and $V_2$ can be recomputed using Kirchoff's Voltage Law, as follows:

$V_1 = I_1 R_1 + V_C = (2.33 \text{ mA})(0.6 \text{ k}\Omega) + 0.7V = 1.4V + 0.7V = 2.1V$ $V_2 = I_2 R_2 + V_C = (1.17 \text{ mA})(0.5 \text{ k}\Omega) + 0.7V = 0.58V + 0.7V = 1.28V$ The above examples illustrate how a specific current distribution on three active electrodes can be achieved and maintained by adjusting voltages on each active electrode. A more general example of the resistive network for an n number of active electrodes is shown in FIG. 6. The current-to-voltage relationships for this resistive network are given by:

$$\begin{pmatrix} I_1 \\ I_2 \\ \vdots \\ I_n \end{pmatrix} = \begin{bmatrix} \frac{\beta R_1 - 1}{\beta R_1^2} & \frac{-1}{\beta R_1 R_2} & \cdots & \frac{-1}{\beta R_1 R_n} \\ \frac{-1}{\beta R_2 R_1} & \frac{\beta R_2 - 1}{\beta R_2^2} & & \frac{-1}{\beta R_2 R_n} \\ \vdots & & \ddots & \vdots \\ \frac{-1}{\beta R_n R_1} & \frac{-1}{\beta R_n R_2} & \cdots & \frac{\beta R N - 1}{\beta R_n^2} \end{bmatrix} \times \begin{pmatrix} V_1 \\ V_2 \\ \vdots \\ V_n \end{pmatrix} \quad [6]$$

$$\text{where, } \beta = \sum_{i=1}^{n} \frac{1}{R_i}$$

Writing equation [6] in matrix form provides:

$$\vec{I} = \begin{pmatrix} I_1 \\ I_2 \\ \vdots \\ I_n \end{pmatrix} \quad \overline{A} = \begin{bmatrix} \frac{\beta R_1 - 1}{\beta R_1^2} & \frac{-1}{\beta R_1 R_2} & \cdots & \frac{-1}{\beta R_1 R_n} \\ \frac{-1}{\beta R_2 R_1} & \frac{\beta R_2 - 1}{\beta R_2^2} & & \frac{-1}{\beta R_2 R_n} \\ \vdots & & \ddots & \vdots \\ \frac{-1}{\beta R_n R_1} & \frac{-1}{\beta R_n R_2} & \cdots & \frac{\beta R n - 1}{\beta R_n^2} \end{bmatrix} \quad \vec{V} = \begin{pmatrix} V_1 \\ V_2 \\ \vdots \\ V_n \end{pmatrix} \quad [7]$$

Given a vector of voltages $\vec{V}$ (i.e, a voltage distribution) at the active electrodes, and given a conductance matrix $\overline{A}$ that is a function of the lumped network resistances $R_n$, the corresponding vector of currents $\vec{I}$ (i.e., the current distribution) can be computed. As discussed above, this current-to-voltage relationship accounts for the interaction among electrodes, such that the current to/from a particular electrode depends on the network resistances and the voltages of all active electrodes.

The matrix equation [7] (i.e., $\vec{I} = \overline{A} \times \vec{V}$) allows the distribution of electrode currents $\vec{I}$ to be computed from a given electrode voltage distribution $\vec{V}$. To calculate a distribution of voltages $\vec{V}$ to maintain a desired distribution of currents $\vec{I}$, one might simply try to rearrange the matrix equation [7] to solve for $\vec{V}$ (i.e., $\vec{I} = \overline{A} \times \vec{V}$). For this resistive network, however, the voltage distribution $\vec{V}$ that will achieve the desired distribution of currents $\vec{I}$ is not unique. That is, a desired current distribution $\vec{I}$ can be achieved with an infinite number of voltage distributions $\vec{V}$, which differ only by a constant offset voltage common to all electrodes. Thus, the voltage distribution $\vec{V}$ cannot be computed by rearranging the matrix equation [7], because it is not possible to invert the conductance matrix $\overline{A}$.

It is possible, however, to establish a unique solution by arbitrarily assigning the voltage at one active electrode (e.g., $V_n$ at electrode $E_n$) to a constant, which can be conveniently selected to be zero. Using Kirchhoff's Current Law, the current through active electrode $E_n$ can then be computed as the negative of the sum of currents through the remaining n−1 active electrodes. The modified system of n−1 equations for computing the voltages needed to achieve a desired distribution of currents $\vec{I}$ is:

$$\begin{pmatrix} V_1 \\ V_2 \\ \vdots \\ V_n \end{pmatrix} = \begin{bmatrix} \frac{\beta R_1 - 1}{\beta R_1^2} & \frac{-1}{\beta R_1 R_2} & \cdots & \frac{-1}{\beta R_1 R_{n-1}} \\ \frac{-1}{\beta R_2 R_1} & \frac{\beta R_2 - 1}{\beta R_2^2} & & \frac{-1}{\beta R_2 R_{n-1}} \\ \vdots & & \ddots & \vdots \\ \frac{-1}{\beta R_{n-1} R_1} & \frac{-1}{\beta R_{n-1} R_2} & \cdots & \frac{\beta R_n - 1}{\beta R_{n-1}^2} \end{bmatrix}^{-1} \times \begin{pmatrix} I_1 \\ I_2 \\ \vdots \\ I_n \end{pmatrix} \quad [8]$$

$$\text{where, } \beta = \sum_{i=1}^{n} \frac{1}{R_i}, V_n = 0, I_n = \sum_{i=1}^{n-1} I_i$$

It should be noted that $\beta$ still includes the lumped resistance for electrode $E_n$ even though the system of equations does not include the electrode voltage $V_n$ or the electrode current $I_n$.

Alternatively, a convenient manner in which to establish a unique solution is to assign the common node voltage $V_C$, which is shared by all network resistances, to zero. This constraint directly satisfies Kirchhoff's Current Law at the common node, since the current from the $i^{th}$ electrode is:

$$I_i=(V_i-V_C)/R_i=V_i/R_i \quad [9]$$

The common node voltage $V_C$ will equal zero if:

$$V_C = \frac{\sum_{i=1}^{N} \frac{V_i}{R_i}}{\sum_{i=1}^{N} \frac{1}{R_i}} = 0 \Rightarrow \sum_{i=1}^{N} \frac{V_i}{Ri} = 0 \Rightarrow \sum_{i=1}^{N} Ii = 0 \quad [10]$$

For this special case of $V_C=0$, the conductance matrix $\overline{A}$ simplifies to a diagonal matrix of the reciprocals of the individual network resistances. A unique voltage distribution $\vec{V}$ that achieves a desired current distribution $\vec{I}$ can thus be computed from the following equations:

$$\begin{pmatrix} V_1 \\ V_2 \\ \vdots \\ V_n \end{pmatrix} = \begin{bmatrix} R_1 & 0 & \cdots & 0 \\ 0 & R_2 & & 0 \\ \vdots & & \ddots & \vdots \\ 0 & 0 & \cdots & R_n \end{bmatrix} \times \begin{pmatrix} I_1 \\ I_2 \\ \vdots \\ I_n \end{pmatrix} \sum_{i=1}^{n} \frac{V_i}{R_i} = \sum_{i=1}^{n} I_i = 0 \quad [11]$$

The sum of the computed voltage distribution $\vec{V}$ and any constant offset voltage will also produce the same desired current distribution $\vec{I}$.

While the common node voltage $V_C$ can be measured directly in a lumped resistive network, this voltage is not directly observable in an actual electrode array. This can lead to practical implementation issues, since equation [11] applies only when $V_C=0$, which cannot be directly confirmed. Thus, in actual use, the solution with one of the electrode voltages (i.e., using equation [8]), instead of the common node voltage $V_C$ (i.e., using equation [11]), arbitrarily set to zero may be preferred. The resulting voltage distribution solution obtained from equation [8] can still be shifted by a voltage constant as needed, since this will not affect the desired current distribution $\vec{I}$. Equation [11], however, still provides a useful construct for measuring the current-to-voltage relationship at a specific operating point using voltage or current perturbations across pairs of electrodes, as will be described below.

In order to effectively apply the above solutions, it is necessary to determine the current-to-voltage relationships (and in this case, the network resistances R) amongst all active electrodes. The methods require accurate determinations in order to compute the correct voltage distribution $\vec{V}$. As discussed above, the network resistances can be determined from measured interelectrode impedances between the active electrodes. In particular, electrode pair resistances between all active electrodes can be measured (calculated from a voltage to current ratio or similar method), as shown in the table below:

TABLE 1

| Electrode Pair Measurements | | | | | |
|---|---|---|---|---|---|
| | $E_1$ | $E_2$ | ... | $E_3$ | ... | $En$ |
| $E_1$ | — | $R_{1,2}$ | ... | $R_{1,3}$ | ... | $R_{1,n}$ |
| $E_2$ | — | — | ... | $R_{2,3}$ | ... | $R_{2,n}$ |
| . | — | — | | — | | . |
| . | | | | | | . |
| . | | | | | | . |
| $En$ | — | — | | — | | — |

In this table, the principle of reciprocity applies (i.e., $R_{i,j}=R_{j,i}$), and therefore, only the upper diagonal of Table 1 needs to be populated. The network resistances $R_1, R_2, \ldots R_n$ are related to the measurements in Table 1 by $R_{1,2}=R_1+R_2$, $R_{2,3}=R_2+R_3, \ldots R_{n-1,n}=R_{n-1}+R_n$, or in general, $R_{i,j}=R_i+R_j$. The network resistances for any three electrodes i, j, and k can thus be calculated from the following equations:

$$R_{i,j}=R_i+R_j; \quad [12a]$$

$$R_{i,k}=R_i+R_k; \quad [12b]$$

and $$R_{j,k}=R_j+R_k, \quad [12c]$$

which can be arranged as:

$$R_i = \frac{R_{i,j} + R_{i,k} - R_{j,k}}{2}; \quad [13a]$$

$$R_j = \frac{R_{i,j} + R_{j,k} - R_{i,k}}{2}; \text{ and} \quad [13b]$$

$$R_k = \frac{R_{i,k} + R_{j,k} - R_{i,j}}{2} \quad [13c]$$

If more than three electrodes are active, each combination of three electrodes will yield another set of three calculated network resistances. Thus, an n number of active electrodes will yield (n−2)! calculated values for each network resistance $R_i$. A function (e.g., averaging) can be performed on these (n−2)! values to obtain a single value. Alternatively, fewer electrode pair resistances could be measured to reduce the overall impedance measurement time.

Notably, for a linear resistive network, accurate impedance measurements can be made with only one pair of electrodes active at a time, with all other electrodes being in a high impedance state during the measurement. In this case, for each electrode pair impedance measurement, the voltage level, which is at zero between the measurement, is perturbed and the resulting current measured to obtain the voltage to current ratio, and thus, the interelectrode impedance between the electrode pair. In other words, the impedance measurement is obtained at a voltage operating point of zero; for example, the voltage perturbation can be applied to an electrode in the absence of a stimulation pulse on the electrode.

Figure 7:
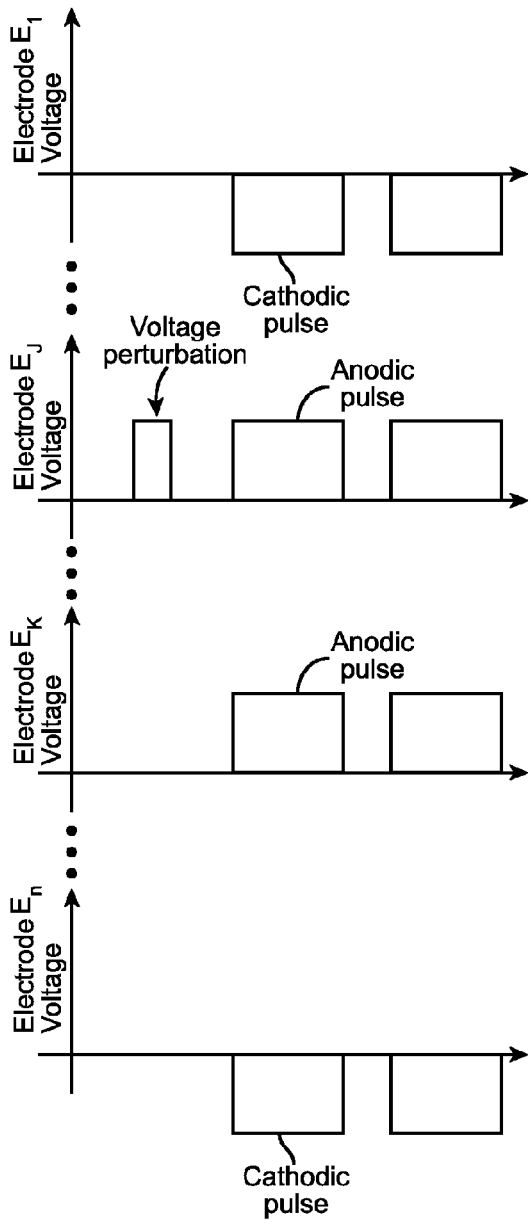
FIG. 7 is a pulse diagram illustrating voltage perturbations and stimulation pulses separately applied by the IPG of FIG. 2 to the resistive network of FIG. 6.

As shown in FIG. 7, a voltage perturbation is generated between electrode $E_j$ and another one of the electrodes, while no stimulation pulses are applied to these electrodes. In the example shown in FIG. 7, a positively polarized voltage perturbation is applied to electrode $E_j$, while the other electrode (e.g., electrode $E_k$) is grounded, with the remaining electrodes being placed in the high impedance state. Alternatively, a negatively polarized voltage perturbation is applied to electrode $E_k$, while the positively polarized voltage perturbation is applied to electrode $E_j$. In any event, a voltage drop is created between electrodes $E_j$ and $E_k$.

It should be noted, however, that an actual electrode array, which exhibits nonlinear behavior at the electrode interface and field interactions among the electrodes, has current-to-voltage relationships that are more complex than those of a linear resistor network. Thus, for more accurate impedance measurements, all electrodes that are active during stimulation should be active during the impedance measurements. In this case, the applied stimulation voltage is perturbed and the resulting current measured to obtain the voltage to current ratio, and thus, the impedance between the electrode pair. In other words, the impedance measurement is obtained at a non-zero voltage operating point; for example, the voltage perturbation can be applied to an electrode in the presence of a stimulation pulse on the electrode.

The perturbation in the applied voltage at an electrode used to make an impedance measurement, however, will change the effective common node voltage $V_C$ in the manner described above. This will cause the other active electrode that is part of the electrode impedance pair to contribute current, thereby distorting the measurement. Thus, an opposite adjustment of the voltage (i.e., a perturbation) on the other electrode in the respective electrode impedance pair during the measurement is needed to null out any change in the common node voltage $V_C$. If there is no change in the effective common node voltage $V_C$, changes in current only occur in the electrode impedance pair, and thus, all other active electrodes that are not part of the electrode pair will not contribute current, and therefore will not distort the measurement.

A convenient aspect of this method is that the ratio of voltage perturbations on the electrode pair required to null out changes in the common node voltage $V_C$ is equal to the ratio of the effective network resistances associated with the electrode pair. These measurements not only yield the interelectrode impedances $R_{j,k}$, but also the network resistances $R_j$ and $R_k$. If $\delta V_j$ is the voltage perturbation on electrode $E_j$, and $\delta V_k$ is the voltage perturbation on electrode $E_k$, then the change in the common node voltage $V_C$ (i.e., $\delta V_C$) will be zero if:

$$\delta V_C = \frac{\sum_{i=1}^{n} \frac{\delta V_i}{R_i}}{\sum_{i=1}^{N} \frac{1}{R_i}} = 0 \Rightarrow \sum_{i=1}^{N} \frac{\delta V_i}{R_i} = 0 \Rightarrow \frac{\delta V_j}{R_j} + \frac{\delta V_k}{R_k} = 0 \Rightarrow \frac{\delta V_j}{R_j} = -\frac{\delta V_k}{R_k} \quad [14]$$

The minus sign in equation [14] exists, because the voltage perturbations $\delta V_j$ and $\delta V_k$ will be opposite in sign to null out any change in $V_C$. The interelectrode impedance measurement $R_{j,k}$ is computed as the change in voltage drop $\delta V_j - \delta V_k$ divided by the change in current (i.e., the current perturbation) $\delta I_{j,k}$ flowing between electrodes $E_j$ and $E_k$. The interelectrode impedance $R_{j,k}$ and the network resistances $R_j$ and $R_k$ can, thus, be calculated from the voltage perturbations $\delta V_j$, $\delta V_k$ and current perturbation $\delta I_{j,k}$ as:

$$R_{j,k} = \frac{\delta V_j - \delta V_k}{\delta I_{j,k}} \quad [15a]$$

$$R_j = \frac{\delta V_j}{\delta I_{j,k}} \quad [15b]$$

$$R_k = -\frac{\delta V_k}{\delta I_{j,k}} \quad [15c]$$

For an n number of electrodes with 1+2+ ... n−1 electrode pair resistances, this method yields n−1 values for each network resistance $R_i$, which could be used in addition to, or instead of, or to confirm, the (n−2)! values computed from combinations of electrode pair resistance triplets discussed above. Alternatively, a perturbation technique can be used to compute the electrode pair resistance triplets, which is advantageous, because the common node voltage $V_C$ need not be maintained at zero, as described in further detail below.

Figure 8:
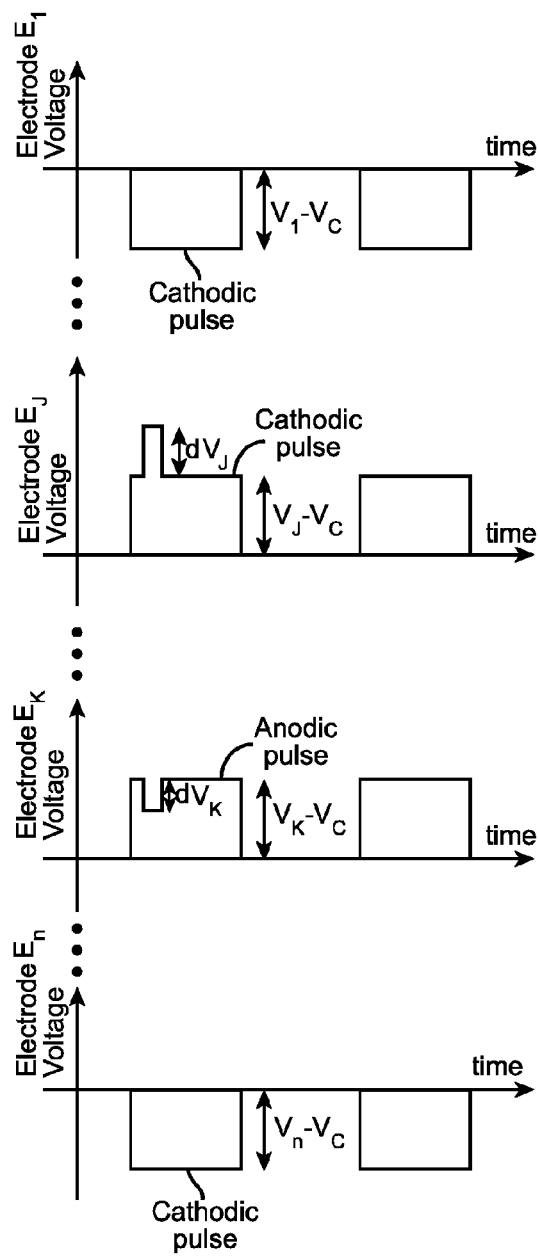
FIG. 8 is a pulse diagram illustrating voltage perturbations and stimulation pulses simultaneously applied by the implantable pulse generator to the resistive network of FIG. 6.

An exemplary applied voltage waveform distribution versus the common node voltage $V_C$ during such a perturbation measurement is shown in FIG. 8. A perturbation current $\delta I_{j,k}$ would only be seen on electrodes $E_j$ and $E_k$ when the voltage perturbations $\delta V_j$ and $\delta V_k$ are balanced to null out or minimize the change in the common node voltage $\delta V_C$. No perturbation current would be seen on the other electrodes. It should be noted that although the voltage perturbations $\delta V_j$ and $\delta V_k$ are shown at the beginning of the stimulation pulses, the voltage perturbations may be applied to the electrodes at any time during the stimulation pulses. The common node voltage can be nulled out minimized by iteratively selecting different ratios of $\delta V_j$ and $\delta V_k$ ($V_k$ can be fixed, while changing $V_j$ to obtain the different ratios).

Using the perturbation voltages $\delta V_j$ and $\delta V_k$ during the stimulation pulse for the interelectrode impedance measurement effectively linearizes the network resistance at the relevent operating point in the system. Thus, the voltage distribution needed to achieve or maintain a desired current distribution can be computed for an electrode array with complex and/or non-linear current-to-voltage relationships. Periodic measurements allow the system to track changes in these relationships over time. Such periodic measurements do not have to occur at every stimulation pulse, as illustrated in FIG. 8. This linearization technique would be more stable when the changes in the desired current distribution are smaller. Such is the case for typical current steering scenarios where it already desirable to make only small changes in the stimulation field to optimize stimulation targeting and maintain patient comfort.

While the methods disclosed herein for estimating network resistances is intended to primarily achieve or maintain a desired distribution of currents using independent voltage-regulated outputs, it has other useful clinical applications. For example, the perturbation method described to measure and calculate the network resistances could be used to provide a numerical and/or graphical display of the impedance of each individual electrode instead of the impedance between two or more electrodes, which may include the IPG case. Because the network resistance is purely associated with a single electrode and not contaminated with information from other electrodes (i.e., it is a pure lumped value that is not affected by the other electrodes), it can be used clinically as a more definitive assessment of the tissue characteristic near the specific electrode. Furthermore, the technique for estimating network resistances is not limited to systems based on multiple independent voltage sources. Current perturbations $\delta I_j$ and $\delta I_k$ in a multiple output constant current system could be used to null out the effective common node voltage $V_C$ as well. The current perturbation ratio $\delta I_j/\delta I_k$ would then also lead to accurate estimates of the current-to-voltage relationship at any desired stimulation operating point.

Although the current-to-voltage relationship has been described as being estimated using network resistances, this relationship may be estimated using other electrical parameters. For example, the current-to-voltage relationship can be estimated using measured field potentials and monopolar electrode impedances. Notably, measured field potential capture information that cannot be captured in the lumped resistor model. As will be described in further detail below, the field potential data for the active electrodes can be arranged in a matrix $\overline{M}$ and the desired currents can be arranged into a vector of currents $\vec{I}$ (i.e., a current distribution), such that multiplication of the current distribution $\vec{I}$ results in a vector of voltages $\vec{V}$ (i.e., a voltage distribution) required to yield the desired currents.

In particular, assuming a resistive medium, when a current is passed between a source electrode and a return electrode, a field potential FP is impressed on all other active electrodes in proximity to the source electrode. These potentials represent or describe the electrical relationship of the medium between the source electrode and a given electrode. The voltage on the source electrode describes the local electrical relationship between that electrode and the medium in the form of an impedance ($V_{meas}/I_{source}$) assuming a "far away" return electrode. The field potentials in the system are linear and superimposable, such that if the field potentials between all sets of two active electrodes (including an electrode and itself, which is presented as a monopolar impedance) are known, the voltage distribution for the active electrodes can be determined for any desired current distribution on the electrodes. The interpretation of this solution can be modified to state: for a desired set of currents, the relative voltages on the active electrodes to achieve those currents can be determined using the known field potential relationships between electrodes.

Relative voltages (and not absolute voltages) are emphasized in this solution, because the solution is not unique, and the solutions differ by an arbitrary offset voltage. That is:

$$\vec{J}_r \propto \Delta V_r = \Delta(Vr + \Phi_{global\ scalar}), \quad [16]$$

where $J_r$ is the current density, $V_r$ is the voltage, and $\Phi_{global\ scalar}$ is a voltage offset added to all points in space.

Given a current distribution $\vec{I}$ for the electrodes, and given a given field potential matrix $\overline{M}$, the corresponding voltage distribution $\vec{V}$ for the electrodes can be computed using the matrix equation $\vec{V} = \overline{M} \times \vec{I}$, which can be expanded as follows:

$$\begin{pmatrix} V_1 \\ V_2 \\ \vdots \\ V_n \end{pmatrix} = \begin{bmatrix} R_1 & FP_{1,2} & FP_{1,3} & \ldots & FP_{1,n} \\ FP_{1,2} & R_2 & FP_{2,3} & \ldots & FP_{2,n} \\ FP_{1,3} & FP_{2,3} & R_3 & \ldots & FP_{3,n} \\ \vdots & \vdots & & \ddots & \\ FP_{1,n} & FP_{2,n} & FP_{3,n} & \ldots & R_n \end{bmatrix} \times \begin{pmatrix} I_1 \\ I_2 \\ \vdots \\ I_n \end{pmatrix}, \quad [17]$$

where $R_i$ is the monopolar impedance at electrode $E_i$ (equal to the field potential at electrode $E_i$ due to unit current at electrode $E_i$), and $FP_{i,j}$ is the field potential at electrode $E_i$ due to unit current at electrode $E_j$ (or vice versa, since the principle of reciprocity applies (i.e., $FP_{i,j} = FP_{j,i}$).

It should be noted that the main assumption in this solution is that the monopolar return electrode is far enough that the current sink/source at the return electrode does not yield significant field potentials at the electrodes on the lead (that is, the return electrode can reasonably be assumed to be at infinity). Furthermore, the resulting voltages rely both on the monopolar impedances, which are expected to be influenced mostly by local properties of the medium, and field potentials, which capture the electrical relationships between the electrodes and are believed to be less dependent on local properties.

A simple two-dimensional volume conductor model consisting of three electrodes was generated to illustrate the solution provided by equation [17]. Monopolar impedances were measured using a "far away" boundary as the return electrode. Using this model, a matrix $\overline{M}$ was generated, as follows:

| 282.44 | 186.57 | 188 |
|---|---|---|
| 186.57 | 251.64 | 189.16 |
| 188 | 189.16 | 235.93 |

If the desired current distribution $\vec{I_{desired}}$ is:

| −1 |
|---|
| 0.75 |
| 0.25 | then equation [17] yields a calculated voltage distribution $\vec{V_{calc}}$ of:

| −95.155 |
|---|
| 33.83 |
| 24.545 |

Recall that the relative voltages, or voltage differences, are the important feature for determining the current distribution on the electrodes, so generally, the calculated voltage distribution $\vec{V}_{calc}$ is:

| $V_{scalar}$ |
|---|
| $V_{scalar} + 144.9625$ |
| $V_{scalar} + 108.365$ | where $V_{scalar}$ is a scalar voltage that assumes the rest of the system is floating.

When the current-regulated boundary conditions were implemented in the model, the modeled solution showed that the voltage distribution $\vec{V}_{model}$ needed to generate the desired current distribution $\vec{I_{desired}}$ is:

| |
|---|
| 14.12 |
| 159.09 |
| 122.49 |

It should be noted that this model does not have a unique solution, since any global scalar offset can be applied to the voltage in space, and the Poisson equation still holds. Generalizing the offset voltage provides the following modeled voltage distribution $\vec{V_{model}}$:

| |
|---|
| $V_{scalar}$ |
| $V_{scalar} + 144.97$ |
| $V_{scalar} + 108.37$ |

Note that the above solution is very near the solution calculated from the matrix equation, and the discrepancy between the modeled voltage distribution $\vec{V_{model}}$ and the calculated voltage distribution $\vec{V_{calc}}$ is accounted for by the effect of the return electrode used to make the monopolar measurements. The discrepancy is low because the reference is "far away" and impresses very small voltages on the electrodes on the lead.

As equation [17] implies, the conversion from a desired current distribution to a voltage distribution is dependent on the accuracy of the matrix $\overline{M}$. Because impedances may change over time, it may be appropriate to automatically update the matrix $\overline{M}$. As an example, if the monopolar impedance of electrode $E_3$ is increased to 400 ohms (e.g., as a result of a tissue encapsulation process), the new matrix $\overline{M}$ will be:

| 282.44 | 186.57 | 188 |
|---|---|---|
| 186.57 | 251.64 | 189.16 |
| 188 | 189.16 | 400 |

If the desired current distribution $\vec{I_{desired}}$ remains the same, then equation [17] yields a calculated voltage distribution $\vec{V_{calc}}$ of:

| |
|---|
| $V_{scalar}$ |
| $V_{scalar} + 144.9625$ |
| $V_{scalar} + 149.3825$ |

As can be seen, this new voltage distribution represents a substantial change from the original voltage distribution. Therefore, automatic adjustment of the matrix $\overline{M}$ would be preferable to maintain the desired current distribution as the impedance change occurs.

Notably, the formulation of equation [17] does not include electrode polarization and output capacitance, which suggests that the analysis is more accurate for short pulses than long pulses. Polarization would be expected to affect the diagonal of the matrix $\overline{M}$ (i.e., the monopolar impedances) and reasonable estimates of the effect of the polarization might be used to change the matrix $\overline{M}$ during a pulse if the current amplitude is to be maintained throughout the pulse. In the same manner described above with the lumped resistor technique, the monopolar impedances and field potentials can be more accurately measured at a non-zero voltage operating point. For example, the voltage perturbation can be applied to an electrode in the presence of a stimulation pulse on the respective electrode. In this case, the monopolar impedance at the specific operating point can be provided by: $R_i=\delta V_i/\delta I_i$, where $R_i$ is the monopolar resistance at active electrode $E_i$, $\delta V_i$ is the voltage perturbation at active electrode $E_i$, and $\delta I_i$ is the current perturbation at active electrode $E_i$. The field potential at the specific operating point can be provided by: $FP_{i,j}=\delta V_j/\delta I_i$, where $FP_{i,j}$ is the field potential at electrode $E_j$ when a voltage perturbation is applied to active electrode $E_i$, $\delta V_j$ is the change in voltage at electrode $E_j$, $\delta I_i$ is the current perturbation at active electrode $E_i$.

Figure 9:
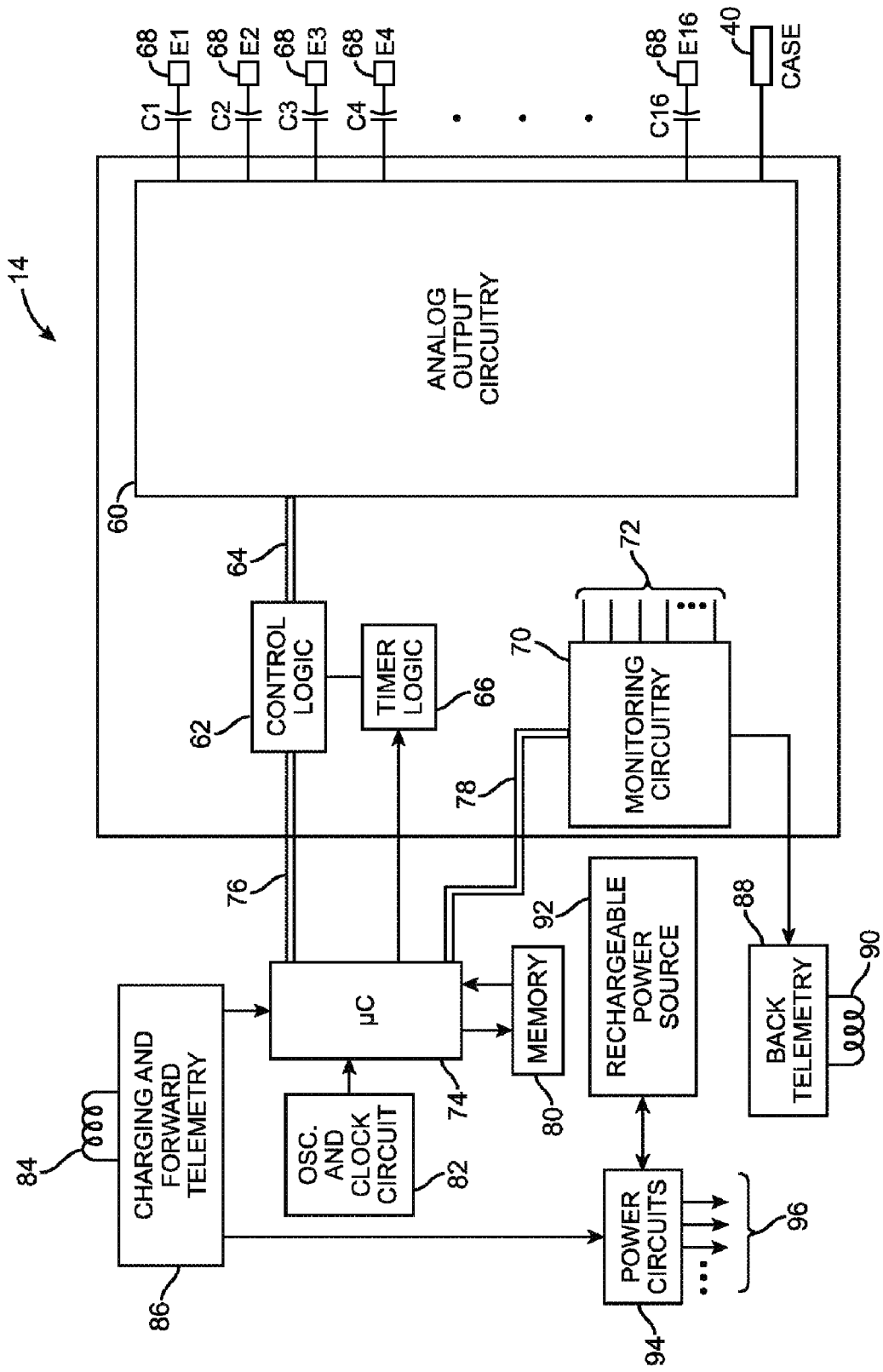
FIG. 9 is a block diagram of the internal components of the IPG of FIG. 2.

Turning next to FIG. 9, the main internal components of the IPG 14 will now be described. The IPG 14 includes analog output circuitry 60 configured for generating electrical stimulation energy in accordance with a defined pulsed waveform having a specified pulse amplitude, pulse rate, and pulse width under control of control logic 62 over data bus 64. Control of the pulse rate and pulse width of the electrical waveform is facilitated by timer logic circuitry 66, which may have a suitable resolution, e.g., 10 μs. The stimulation energy generated by the analog output circuitry 60 is output via capacitors C1-C16 to electrical terminals 68 corresponding to electrodes E1-E16.

The analog output circuitry 60 comprises independently controlled voltage sources for providing stimulation pulses of a specified and known voltage at the electrodes 26. The operation of this analog output circuitry 60, including alternative embodiments of suitable output circuitry for performing the same function of generating voltage regulated stimulation pulses of a prescribed amplitude and width, is described more fully in U.S. Pat. Nos. 6,516,227 and 6,993,384, which are expressly incorporated herein by reference.

Figure 10A:
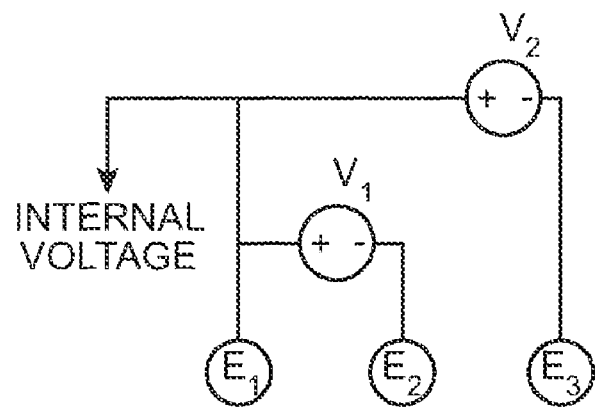
FIG. 10a-10c are circuit diagrams illustrating various voltage source arrangements that can be used in the analog output circuitry of the IPG of FIG. 2.
Figure 10B:
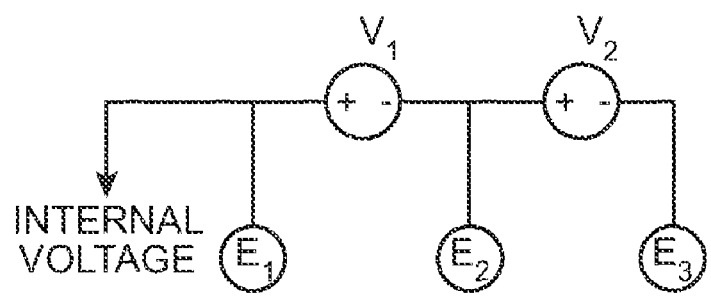
Figure 10C:
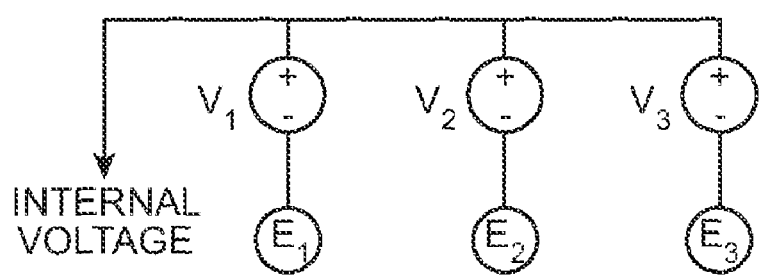

Notably, because the relative outputs of the voltage sources are the critical consideration for establishing the desired current distribution on the activated ones of the electrodes E1-E16, and thus the offset voltage for the voltage sources can take any reasonable value, several voltage source configurations may be implemented within the analog output circuitry 60 to achieve the desired current distribution, as shown in FIGS. 10a-10c.

The voltage source configurations shown in FIGS. 10a and 10b advantageously uses fewer voltage sources (only two voltage sources V1 and V2 for three electrodes $E_1$, $E_2$, and $E_3$) by setting one of the electrodes (in this case, electrode $E_1$) to an internal reference voltage, while the voltage source configuration shown in FIG. 10c uses an additional voltage source (and in particular, three voltage sources $V_1$, $V_2$, and $V_3$ tied to an internal reference), but advantageously requires smaller absolute voltage excursions from an internal reference voltage For example, assuming that it is desired to apply voltage values of $V_C$, 145, and 149 respectively at electrodes $E_1$, $E_2$, and $E_3$, the following values for the voltage sources are needed. In particular, for the voltage source configuration of FIG. 10a, the $V_1=V_C-145$ and $V_2=V_C-149$; for the voltage source configuration of FIG. 10b, $V_1=V_C-145$ and $V_2=V_1-149=(145-V_C)-149=V_C-4$; and for the voltage source configuration of FIG. 10c, $V_1=-V_C$, $V_2=V_C-145$, and $V_3=V_C-149$. It can be recognized that the voltage source configurations of FIGS. 10a and 10b are representative those configurations that couple an electrode directly to an internal reference, and the voltage source configuration of FIG. 10c is representative of those that that do not couple an electrode directly to an internal reference and require an additional voltage source.

The IPG 14 further comprises monitoring circuitry 70 for monitoring the status of various nodes or other points 60 throughout the IPG 14, e.g., power supply voltages, temperature, battery voltage, and the like. Notably, the electrodes 26 fit snugly within the epidural space of the spinal column, and because the tissue is conductive, electrical measurements can be taken between the electrodes 26. Significantly, the monitoring circuitry 70 is configured for taking such electrical measurements (e.g., interelectrode impedance, monopolar impedance, and field potential), so that, in addition to performing fault detection between the electrodes 26 and the analog output circuitry 60 and determining the coupling efficiency between the electrodes 26 and the tissue in a conventional manner, the CP 18 can achieve and maintain a desired current distribution on the active electrodes 26 by adjusting the voltages on the active electrodes 26, as described in detail above. Measurement of the electrical parameter data, such as electrode impedance and field potential, also facilitates lead migration detection, as described in U.S. patent application Ser. No. 11/938,490, entitled "Apparatus and Method for Determining the Relative Position and Orientation of Neurostimulation Leads," which is expressly incorporated herein by reference.

Electrical parameter data can be measured using any one of a variety means. For example, the electrical parameter data measurements can be made on a sampled basis during a portion of the time while the electrical stimulus pulse is being applied to the tissue (e.g., if the required voltage distribution necessary to achieve the desired current distribution is to be estimated at a non-zero operating point of the stimulation), as described in U.S. Pat. No. 7,317,948, which is expressly incorporated herein by reference. Alternatively, the electrical parameter data measurements can be made independently of the electrical stimulation pulses (e.g., if the required voltage distribution necessary to achieve the desired current distribution is to be estimated at a zero operating point of the stimulation), such as described in U.S. Pat. Nos. 6,516,227 and 6,993,384, which are expressly incorporated herein by reference.

One impedance measurement technique may be performed by measuring impedance vectors, which can be defined as impedance values measured between selected pairs of electrodes 26. The interelectrode impedance may be determined in various ways. For example, because the analog output circuitry 60 sources voltage, a known voltage can be applied between a pair of electrodes 26, the current between the electrodes 26 can be measured, and the impedance between the electrodes 26 can be calculated as a ratio of the known voltage to measured current.

The field potential technique may be performed by generating an electrical field at selected ones of the electrodes 26 and recording the electrical field at other selected ones of the lead electrodes 26. This may be accomplished in one of a variety of manners. For example, an electrical field may be generated conveying electrical energy to a selected one of the electrodes 26 and returning the electrical energy at the IPG case 40. Alternatively, multipolar configurations (e.g., bipolar or tripolar) may be created between the lead electrodes 26. Or, an electrode that is sutured (or otherwise permanently or temporarily attached (e.g., an adhesive or gel-based electrode) anywhere on the patient's body may be used in place of the case IPG outer case 40 or lead electrodes 26. In either case, while a selected one of the electrodes 26 is activated to generate the electrical field, a selected one of the electrodes 26 (different from the activated electrode) is operated to record the voltage potential of the electrical field.

Further details discussing the measurement of electrical parameter data, such as electrode impedance and field potential, are described in U.S. patent application Ser. No. 11/938, 490, entitled "Apparatus and Method for Determining the Relative Position and Orientation of Neurostimulation Leads," which has previously been incorporated herein by reference.

The IPG 14 further comprises processing circuitry in the form of a microcontroller (µC) 74 that controls the control logic 62 over data bus 76, and obtains status data from the monitoring circuitry 70 via data bus 78. The IPG 14 further comprises memory 80 and oscillator and clock circuit 82 coupled to the µC 74. The µC 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the µC 74 generates the necessary control and status signals, which allow the µC 74 to control the operation of the IPG 14 in accordance with a selected operating program and stimulation parameters. In controlling the operation of the IPG 14, the µC 74 is able to individually generate stimulus pulses at the electrical terminals 68 using the analog output circuitry 60, in combination with the control logic 62 and timer logic circuitry 66, thereby allowing each electrical terminal 68 to be paired or grouped with other electrical terminals 68, including the monopolar case electrode, to control the polarity, amplitude, rate, pulse width, pulse shape, and channel through which the current stimulus pulses are provided. The µC 74 facilitates the storage of electrical parameter data measured by the monitoring circuitry 70 within memory 80.

The IPG 14 further comprises a receiving coil 84 for receiving programming data (e.g., the operating program and/or stimulation parameters) from the external programmer (i.e., the RC 16 or CP 18) in an appropriate modulated carrier signal, and charging, and circuitry 86 for demodulating the carrier signal it receives through the receiving coil 84 to recover the programming data, which programming data is then stored within the memory 80, or within other memory elements (not shown) distributed throughout the IPG 14.

The IPG 14 further comprises back telemetry circuitry 88 and a transmission coil 90 for sending informational data to the external programmer. The back telemetry features of the IPG 14 also allow its status to be checked. For example, when the CP 18 initiates a programming session with the IPG 14, the capacity of the battery is telemetered, so that the CP 18 can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 92 and power circuits 94 for providing the operating power to the IPG 14. The rechargeable power source 92 may, e.g., comprise a lithium-ion or lithium-ion polymer battery or other form of rechargeable power. The rechargeable source 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the receiving coil 84.

To recharge the power source 92, the external charger 22 (shown in FIG. 1), which generates the AC magnetic field, is placed against, or otherwise adjacent, to the patient's skin over the implanted IPG 14. The AC magnetic field emitted by the external charger induces AC currents in the receiving coil 84. The charging and forward telemetry circuitry 86 rectifies the AC current to produce DC current, which is used to charge the power source 92. While the receiving coil 84 is described as being used for both wirelessly receiving communications (e.g., programming and control data) and charging energy from the external device, it should be appreciated that the receiving coil 84 can be arranged as a dedicated charging coil, while another coil, such as the coil 90, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference.

It should be noted that rather than an IPG, the SCS system 10 may alternatively utilize an implantable receiver-stimulator (not shown) connected to the stimulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 11:
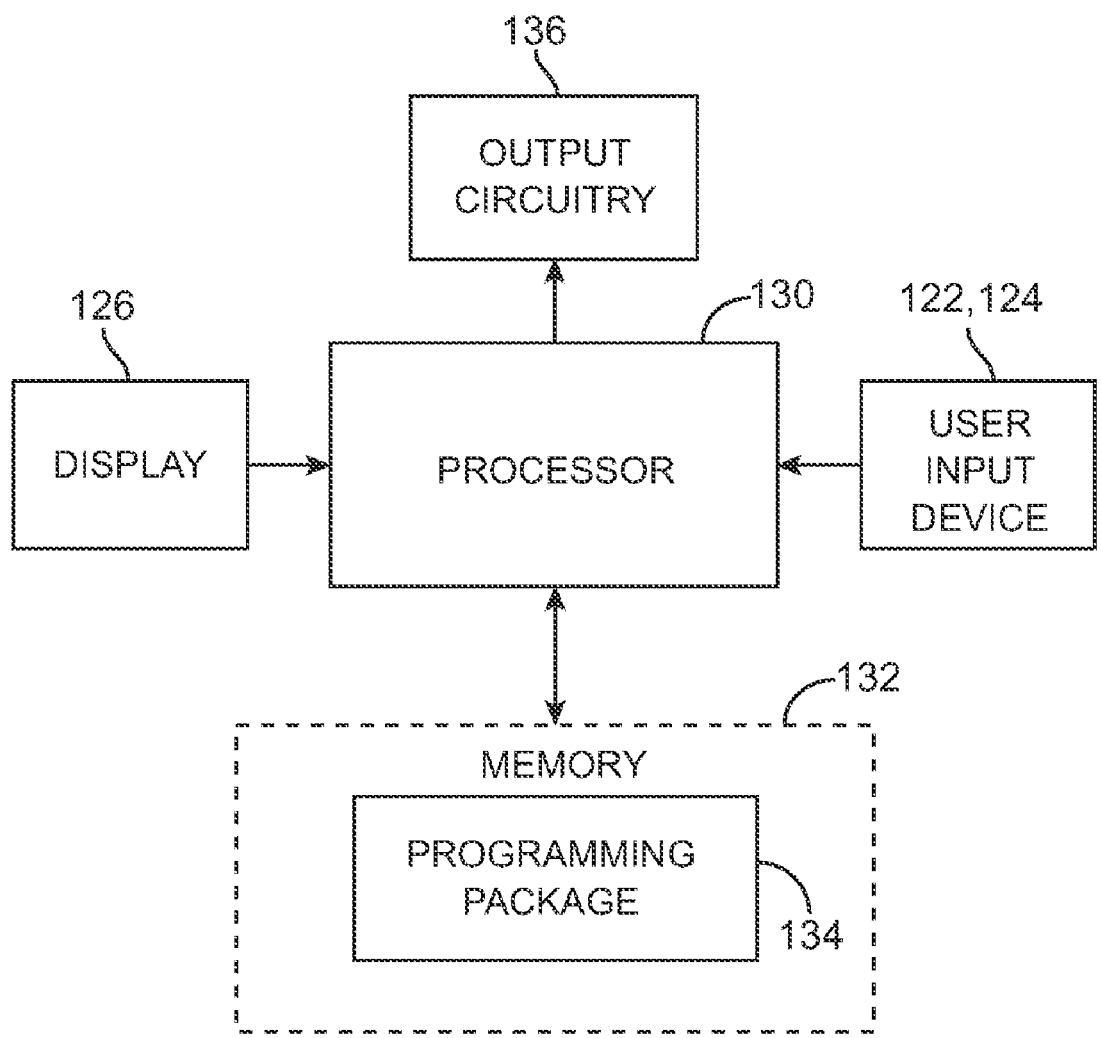
FIG. 11 is a plan view of a remote control that can be used in the SCS system of FIG. 1.

Referring now to FIG. 11, one exemplary embodiment of an RC 16 will now be described. As previously discussed, the RC 16 is capable of communicating with the IPG 14 or CP 18. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate. For example, the selection button 108 can be actuated to place the RC 16 in an "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112.

Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 12:
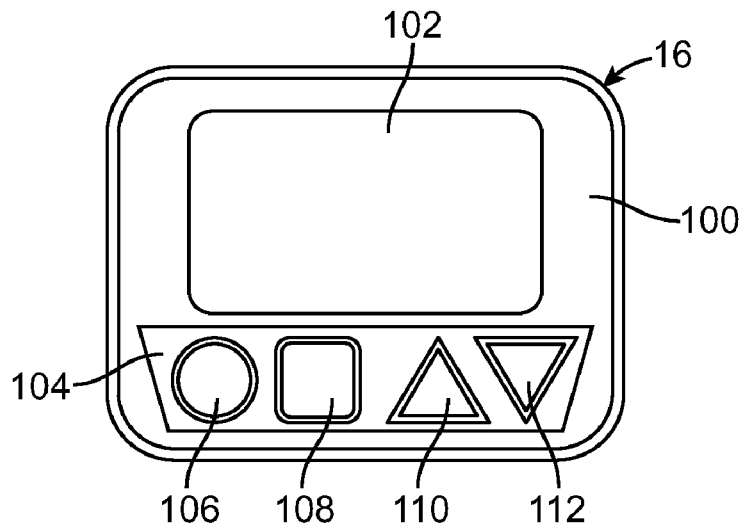
FIG. 12 is a block diagram of the internal componentry of the remote control of FIG. 11.

Referring to FIG. 12, the internal components of an exemplary RC 16 will now be described. The RC 16 generally includes a processor 114 (e.g., a microcontroller), memory 16 that stores an operating program for execution by the processor 114, as well as stimulation parameter sets (which can be generated from a look-up table or a formula), input/output circuitry, and in particular, telemetry circuitry 118 for outputting stimulation parameters to the IPG 14 and receiving status information from the IPG 14, and input/output circuitry 120 for receiving stimulation control signals from the button pad 104 and transmitting status information to the display screen 102 (shown in FIG. 11). As well as controlling other functions of the RC 16, which will not be described herein for purposes of brevity, the processor 114 generates new stimulation parameter sets in response to the user operation of the button pad 104. These new stimulation parameter sets would then be transmitted to the IPG 14 via the telemetry circuitry 118. Further details discussing the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 near the spinal cord.

As shown in FIG. 3, the overall appearance of the CP 18 is that of a laptop personal computer (PC), and in fact, may be implemented using a PC that has been appropriately configured to include a directional-programming device and programmed to perform the functions described herein. Thus, the programming methodologies can be performed by executing software instructions contained within the CP 18. More significant to the present inventions, the software instructions can be executed within the CP 18 to perform the electrode current-voltage relationship determination and voltage distribution estimation techniques described herein and to generate the stimulation parameters corresponding to the estimated voltage distribution. Alternatively, such programming methodologies can be performed using firmware or hardware. In any event, the CP 18, under the control of the clinician, may actively control the characteristics of the electrical stimulation generated by the IPG 14 (including performing current steering via the voltage-regulated circuitry contained within the IPG 14 and/or changing the total current flowing through the active electrodes) to allow the optimum stimulation parameters to be determined based on patient feedback and for subsequently programming the IPG 14 with the optimum stimulation parameters.

Figure 13:
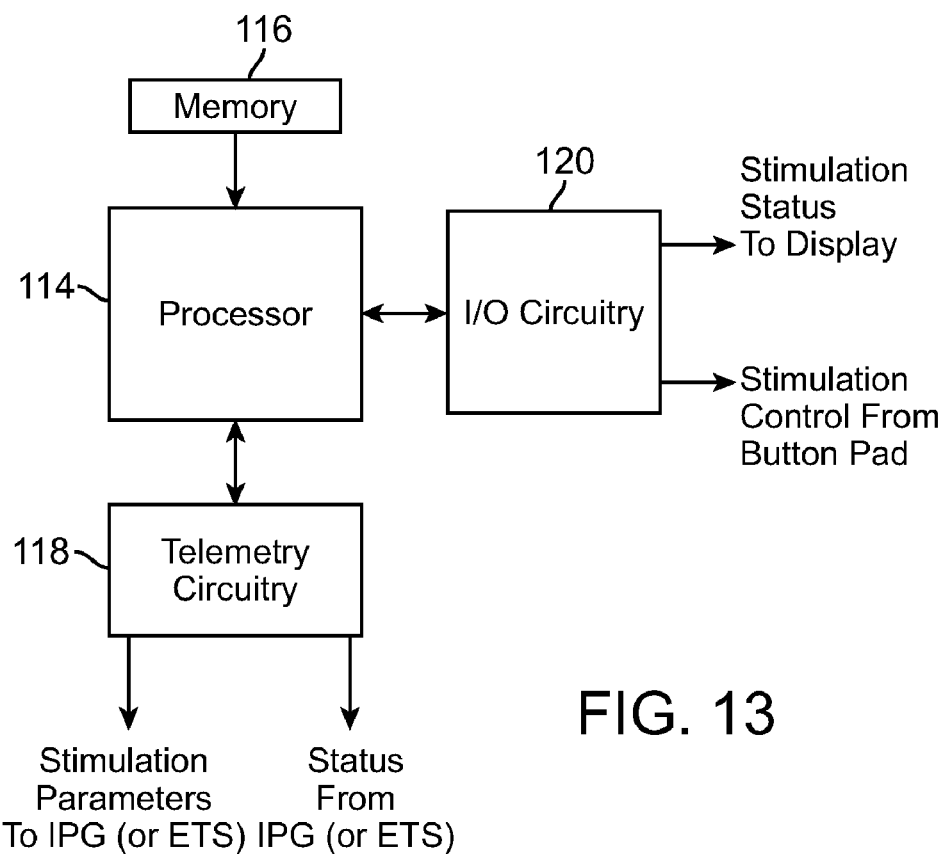
FIG. 13 is a block diagram of the components of a computerized programming system that can be used in the SCS system of FIG. 1.

As shown in FIG. 13, the CP 18 generally includes a processor 130 (e.g., a central processor unit (CPU)) and memory 132 that stores a stimulation programming package 134, which can be executed by the processor 130 to allow a clinician to program the IPG 14 and RC 16. In performing this function, the processor 130 generates a plurality of stimulation parameter sets from the parameter values manually varied by the user via operation of the user input device 122, 124, or otherwise automatically varied by the processor 130 itself. In any event, during current steering or an increase/decrease in the total current flowing through the active electrodes, the processor 130 will generate the stimulation parameters in accordance with the estimated voltage distribution necessary to achieve the desired current distribution in the manner described above. The CP 18 further includes output circuitry 136 (e.g., via the telemetry circuitry of the RC 16) for downloading stimulation parameters to the IPG 14 and RC 16 and for uploading stimulation parameters already stored in the memory 116 of the RC 16, as well as electrical parameters measured by the IPG 14, via the telemetry circuitry 118 of the RC 16. To allow the clinician to perform these functions, the CP 18 includes a user input device (e.g., a mouse 122 and keyboard 124 shown in FIG. 3), and a display monitor 126 housed in a case 128 (also shown in FIG. 3).

Further details discussing user interfaces and exemplary stimulation programming packages are described in U.S. Pat. No. 6,393,325 and U.S. Patent Application Ser. No. 61/080, 187, entitled "System and Method for Converting Tissue Stimulation Programs in a Format Usable by an Electrical Current Steering Navigator," which are expressly incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of performing a medical procedure using a plurality of electrodes implanted within tissue of a patient, comprising:
generating an electrical energy perturbation on at least one of the plurality of electrodes; and
computing network resistances for each of at least three active ones of the electrodes in response to the electrical energy perturbation, wherein the network resistances represent the resistances between the respective active electrodes and a common node to which the active electrodes are connected in parallel.

2. The method of claim 1, wherein the electrical energy perturbation is a voltage-regulated perturbation.

3. The method of claim 1, wherein the electrical energy perturbation creates a change in voltage drop between two of the active electrodes and a change in electrical current between the two active electrodes, and wherein the computation of the network resistance for each of the two active electrodes comprises dividing a change in voltage on the respective active electrode by the change in the electrical current between the two electrodes.

4. The method of claim 3, wherein the change in voltage drop between the two active electrodes maintains a voltage at the common node at the same value.

5. The method of claim 4, wherein the generation of the electrical energy perturbation comprises generating oppositely polarized pulses at the two active electrodes.

6. The method of claim 1, further comprising measuring interelectrode impedances between the active electrodes in response to generating the electrical energy perturbation, wherein the network resistances are computed based on the measured interelectrode impedances.

7. The method of claim 6, wherein each interelectrode impedance for a respective active electrode is computed by summing interelectrode impedances between each respective active electrode and two of the other active electrodes, subtracting the interelectrode impedance between the other two active electrodes from the sum, and dividing the result by two.

8. The method of claim 1, further comprising determining an electrical voltage distribution on the active electrodes necessary to achieve a desired electrical current distribution on the active electrodes, or determining an electrical current distribution on the active electrodes necessary to achieve a desired voltage distribution on the active electrodes, wherein the electrical voltage distribution or electrical current distribution is based on the computed network resistances.

9. The method of claim 1, further comprising conveying electrical stimulation energy between the active electrodes and the tissue, wherein the network resistances are computed at a zero operating point of the conveyed electrical stimulation energy.

10. The method of claim 9, wherein the electrical energy perturbation is generated in the absence of the conveyed electrical stimulation energy.

11. The method of claim 1, further comprising conveying electrical stimulation energy between the active electrodes and the tissue, wherein the network resistances are computed at a non-zero operating point of the conveyed electrical stimulation energy.

12. The method of claim 11, wherein the electrical energy perturbation is generated during the conveyance of the electrical stimulation energy.

13. A neurostimulation system, comprising:
a plurality of electrodes configured for being placed in contact with tissue;
analog output circuitry configured generating an electrical energy perturbation on at least one of the plurality of electrodes; and
processing circuitry configured for computing network resistances for each of at least three active ones of electrodes in response to the electrical energy perturbation, wherein the network resistances represent the resistances between the respective active electrodes and a common node to which the active electrodes are connected in parallel.

14. The neurostimulation system of claim 13, wherein the electrical energy perturbation is a voltage-regulated perturbation.

15. The neurostimulation system of claim 13, wherein the electrical energy perturbation creates a change in voltage drop between two of the active electrodes and a change in electrical current between the two active electrodes, and wherein the processing circuitry is configured for computing the network resistance for each of the two active electrodes by dividing a change in voltage on the respective active electrode by the change in the electrical current between the two active electrodes.

16. The neurostimulation system of claim 15, wherein the change in voltage drop between two of the active electrodes maintains a voltage at the common node at the same value.

17. The neurostimulation system of claim 16, wherein the generation of the electrical energy perturbation comprises generating oppositely polarized pulses at the two active electrodes.

18. The neurostimulation system of claim 13, further comprising monitoring circuitry configured for measuring interelectrode impedances between the active electrodes in response to the analog output circuitry generating the electrical energy perturbation, wherein the processing circuitry is configured for computing the network resistances based on the measured interelectrode impedances.

19. The neurostimulation system of claim 18, wherein the processing circuitry is configured for computing each interelectrode impedance for a respective active electrode by summing interelectrode impedances between each respective active electrode and two of the other active electrodes, subtracting the interelectrode impedance between the other two active electrodes from the sum, and dividing the result by two.

20. The neurostimulation system of claim 13, wherein the processing circuitry is further configured for determining an electrical voltage distribution on the active electrodes necessary to achieve a desired electrical current distribution on the active electrodes, or determining an electrical current distribution on the active electrodes necessary to achieve a desired voltage distribution on the active electrodes, wherein the electrical voltage distribution or electrical current distribution is based on the computed network resistances.

21. The neurostimulation system of claim 13, wherein the analog output circuitry is further configured for conveying electrical stimulation energy between the active electrodes and the tissue, and wherein the processing circuitry is configured for computing the network resistances at a zero operating point of the conveyed electrical stimulation energy.

22. The neurostimulation system of claim 21, wherein the analog output circuitry is configured for generating the electrical energy perturbation in the absence of the conveyed electrical stimulation energy.

23. The neurostimulation system of claim 13, wherein the analog output circuitry is further configured for conveying electrical stimulation energy between the active electrodes and the tissue, and wherein the processing circuitry is configured for computing the network resistances at a non-zero operating point of the conveyed electrical stimulation energy.

24. The neurostimulation system of claim 23, wherein the analog output circuitry is configured for generating the electrical energy perturbation during the conveyance of the electrical stimulation energy.

25. The neurostimulation system of claim 13, further comprising an implantable neurostimulator containing the analog output circuitry, and an external controller containing the processing circuitry.

* * * * *